US011854575B1

(12) United States Patent
Pinkus et al.

(10) Patent No.: US 11,854,575 B1
(45) Date of Patent: Dec. 26, 2023

(54) SYSTEM FOR PRESENTATION OF SENTIMENT DATA

(71) Applicant: AMAZON TECHNOLOGIES, INC., Seattle, WA (US)

(72) Inventors: Alexander Jonathan Pinkus, Seattle, WA (US); Hanhan Wang, Seattle, WA (US); Samuel Elbert McGowan, Seattle, WA (US); Bilyana Slavova, Redmond, WA (US); Narendra Gyanchandani, Sammamish, WA (US); David Cole, Brier, WA (US)

(73) Assignee: AMAZON TECHNOLOGIES, INC., Seattle, WA (US)

( * ) Notice: Subject to any disclaimer, the term of this patent is extended or adjusted under 35 U.S.C. 154(b) by 74 days.

(21) Appl. No.: 16/588,769

(22) Filed: Sep. 30, 2019

(51) Int. Cl.
| | |
|---|---|
| G06F 3/04847 | (2022.01) |
| G10L 25/72 | (2013.01) |
| G10L 25/63 | (2013.01) |
| G06F 1/16 | (2006.01) |
| G06F 3/01 | (2006.01) |
| G06F 3/0481 | (2022.01) |
| G10L 15/26 | (2006.01) |

(52) U.S. Cl.
CPC .............. *G10L 25/72* (2013.01); *G06F 1/163* (2013.01); *G06F 3/011* (2013.01); *G06F 3/0481* (2013.01); *G10L 15/26* (2013.01); *G10L 25/63* (2013.01)

(58) Field of Classification Search
CPC ... G10L 15/26; G10L 25/63; G10L 2015/223; G06F 40/30; G06F 2203/011; G06F 3/167; G06F 16/686; H04M 2203/551; H04M 3/42221; H04M 3/5141; H04M 3/537
See application file for complete search history.

(56) References Cited

U.S. PATENT DOCUMENTS

| | | | |
|---|---|---|---|
| 10,069,971 B1 * | 9/2018 | Shaw .................. | H04M 3/5133 |
| 10,437,332 B1 * | 10/2019 | Paterson ................. | G06F 3/015 |
| 2007/0071206 A1 * | 3/2007 | Gainsboro .............. | G10L 25/63 |
| | | | 379/168 |
| 2008/0059158 A1 * | 3/2008 | Matsuo ................... | H04M 1/21 |
| | | | 704/E11.001 |

(Continued)

OTHER PUBLICATIONS

Kehrein R, "The prosody of authentic emotions", 2002, In Speech Prosody 2002, International Conference 2002, pp. 1-4.*

(Continued)

*Primary Examiner* — Olujimi A Adesanya
(74) *Attorney, Agent, or Firm* — Lindauer Law, PLLC

(57) ABSTRACT

A microphone acquires audio data of a user's speech. The audio data is processed to determine sentiment data indicative of perceived emotional content of the speech. For example, the sentiment data may include values for one or more of valence that is based on a particular change in pitch over time or activation that is based on speech pace. A simplified user interface provides the user with a graphical representation based on the sentiment data and associated descriptors. For example, a visual indicator such as a dot may be shown at particular coordinates onscreen that correspond to the sentiment data. Text descriptors may also be presented near the dot. As the user continues speaking, and new audio data is processed, the interface is dynamically updated. The user may use this information to assess their state of mind, facilitate interactions with others, and so forth.

20 Claims, 13 Drawing Sheets

(56) References Cited

U.S. PATENT DOCUMENTS

| | | | | |
|---|---|---|---|---|
| 2013/0018837 | A1* | 1/2013 | Lee | A61B 5/165 |
| | | | | 706/52 |
| 2013/0080169 | A1* | 3/2013 | Harada | G10L 25/63 |
| | | | | 704/E15.001 |
| 2013/0121591 | A1* | 5/2013 | Hill | G10L 15/1815 |
| | | | | 382/195 |
| 2013/0178962 | A1* | 7/2013 | DiMaria | G06F 3/0482 |
| | | | | 700/94 |
| 2014/0140497 | A1* | 5/2014 | Ripa | H04M 3/5133 |
| | | | | 379/265.06 |
| 2014/0236596 | A1* | 8/2014 | Martinez | G10L 15/26 |
| | | | | 704/235 |
| 2015/0213002 | A1* | 7/2015 | Gou | G06F 16/358 |
| | | | | 704/9 |
| 2015/0256675 | A1* | 9/2015 | Sri | H04M 3/5183 |
| | | | | 379/265.09 |
| 2015/0287402 | A1* | 10/2015 | Okabe | G10L 15/08 |
| | | | | 704/249 |
| 2018/0124243 | A1* | 5/2018 | Zimmerman | H04M 3/5175 |
| 2019/0159716 | A1* | 5/2019 | Alailima | G16H 20/10 |
| 2020/0089767 | A1* | 3/2020 | Ni | G06Q 30/016 |
| 2020/0236211 | A1* | 7/2020 | Taktak | H04M 1/7243 |
| 2021/0034226 | A1* | 2/2021 | Guazzi | G06F 3/04883 |

OTHER PUBLICATIONS

Grimm et al, "Primitives-based evaluation and estimation of emotions in speech", 2007, Speech communication. Oct. 1, 2007;49(10-11):787-800.*

* cited by examiner

600

| DESCRIPTOR LIBRARY 160 ||
|---|---|
| INDEX VALUE 408 | DESCRIPTOR(S) 602 |
| 408(1) | antsy, edgy, perturbed, troubled, ... |
| 408(2) | amazed, astounded, flabbergasted, ... |
| 408(3) | admiring, approving, complimentary, ... |
| 408(4) | uninterested, disinterested, jaded, ... |
| 408(5) | peaceful, placid, serene, tranquil, ... |
| 408(6) | protective, self-protective, ... |
| 408(7) | disgruntled, aggrieved, discontented, ... |
| 408(8) | pleased, jolly, gleeful, ... |

SYSTEM FOR PRESENTATION OF SENTIMENT DATA

BACKGROUND

Participants in a conversation may be affected by the emotional state of one another as perceived by their voice. For example, if a speaker is excited a listener may perceive that excitement in their speech. However, a speaker may not be aware of the emotional state that may be perceived by others as conveyed by their speech.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features.

FIG. 6 is a block diagram of a descriptor library that associates labels in the sentiment data with descriptors for presentation in the user interface, according to one implementation.

Figure 1:
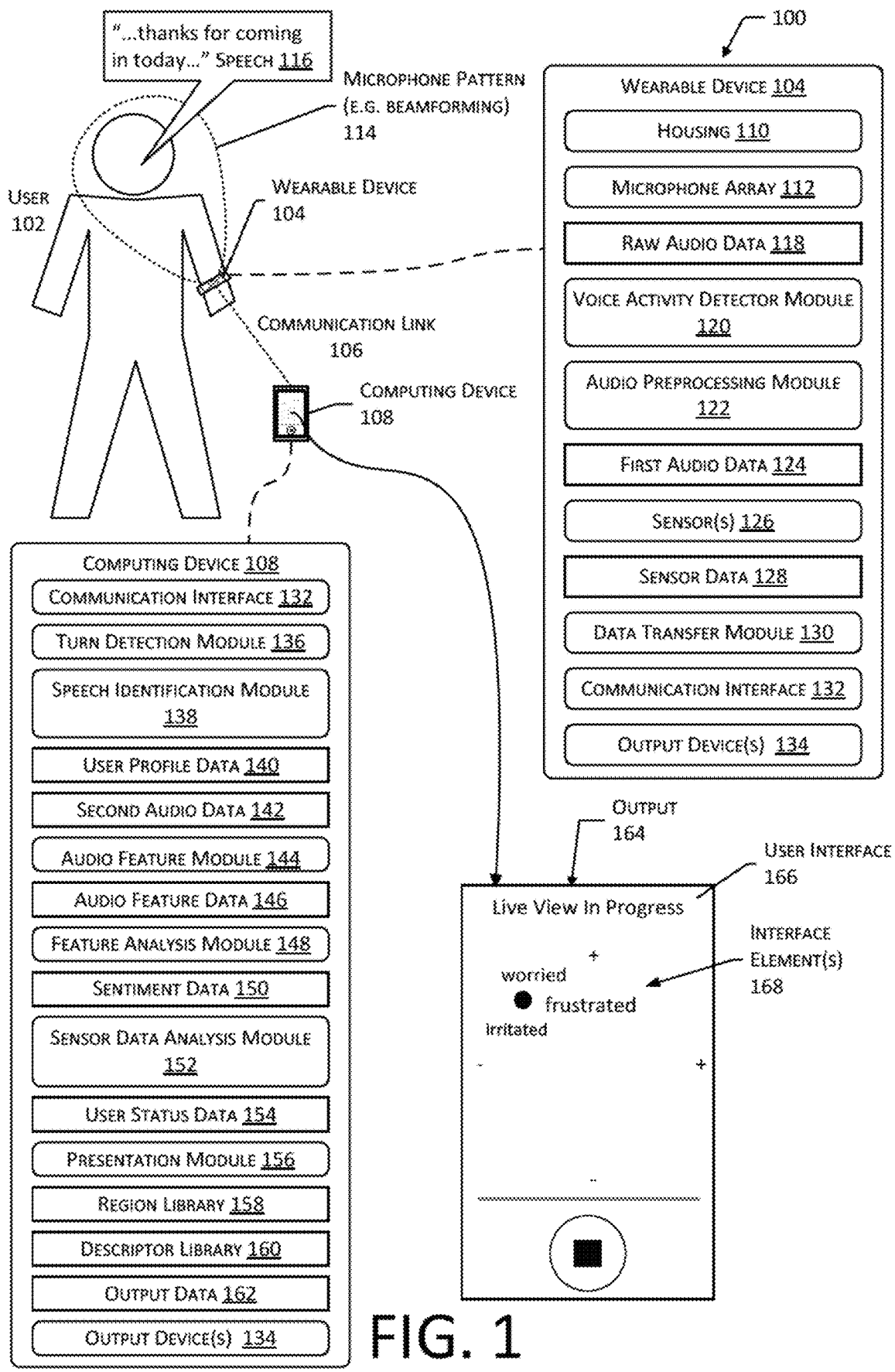
FIG. 1 is an illustrative system that processes speech of a user to determine sentiment data that is indicative of an emotional state as conveyed by the speech and presenting output related to that sentiment data, according to one implementation.

While implementations are described herein by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including, but not limited to.

DETAILED DESCRIPTION

The emotions a person presents to others through their speech are part of the way we communicate with one another. Information about the emotional state that they are expressing may be useful to helping a person better interact with the people around them, improve their relationships with others, and may also improve the person's physical well-being.

Information about someone's emotional state traditionally has been provided by other people. For example, if a person sounds angry while speaking to their friend, the friend may let them know. With that awareness, the angry person may then be able to modify their behavior. As useful as this feedback is, it is infeasible to have a friend constantly present who is able to tell a person what the emotional state expressed in their voice is.

Described in this disclosure is a system for providing a user interface that provides information about a recently presented emotional state. The user authorizes the system to process their speech. For example, the user may enroll in the use, and consent to acquisition and processing of audio of the user speaking. Raw audio as acquired from one or more microphones is processed to provide audio data that is associated with the enrolled user. This audio data is then processed to determine audio feature data. For example, the audio feature data may be processed by a neural network to generate feature vectors representative of the audio data and changes in the audio data. The audio feature data is then processed to determine sentiment data for that particular user. For example, the system discards audio data that is not associated with the particular user and generates the audio feature data from the audio data that is associated with the particular user. After the audio feature data is generated, the audio data of the particular user may be discarded.

A wearable device may be used to acquire the raw audio. For example, the wearable device may comprise a band, bracelet, necklace, earring, brooch, and so forth. The wearable device may comprise one or more microphones and a computing device. The wearable device may be in communication with another device, such as a smartphone. The wearable device may provide audio data to the smartphone for processing. The wearable device may include sensors, such as a heart rate monitor, accelerometer, and so forth. Sensor data obtained by these sensors may be used to determine user status data. For example, accelerometer data may be used to generate user status data indicating how much movement the user has engaged in during the previous day.

In other implementations, the functionality of the system as described may be provided by a single device or distributed across other devices. For example, a server may be accessible via a network to provide some functions that are described herein.

The sentiment data is determined by analyzing characteristics of the user's speech as expressed in the audio feature data. Changes over time in pitch, pace, and so forth may be indicative of various emotional states. For example, the emotional state of speech that is described as "excited" may correspond to speech which has a greater pace while slower paced speech is described as "bored". In another example, an increase in average pitch may be indicative of an emotional state of "angry" while an average pitch that is close to a baseline value may be indicative of an emotional state of "calm". Various techniques may be used individually or in combination to determine the sentiment data including, but not limited to, signal analysis techniques, classifiers, neural networks, and so forth. The sentiment data may be provided as numeric values, vectors, associated labels, and so forth. For example, the sentiment data associated with a particular interval of time may comprise one or more labels indicative of emotional states and values of one or more emotional dimensions, such as an activation value and a valence value.

As the system acquires audio data, the system may provide ongoing output of sentiment data. For example, the system may provide sentiment data for the last turn spoken by the user. In another example, the system may provide sentiment data for the last 500 milliseconds of speech by the user. This provides sentiment data on a near realtime basis which may then be used to provide near realtime output to the user in a user interface.

The user interface may comprise a graphical user interface (GUI) that provides information to the user in a simplified and quick to comprehend fashion. The user interface is designed to provide a dynamic experience, and the output of the user interface may be updated responsive to recently available sentiment data. In one implementation, the user interface facilitates comprehension and allows the user to consistently assess their sentiment by associating particular regions in an emotional space with specified characteristics, such as particular colors. For example, if the emotional space is described by a pair of orthogonal axes, one describing activation values and the other valence values, a region may be described in terms of these two axes. A particular region may be associated with a particular color. The regions may be associated with corresponding areas within a presentation area of the user interface.

During operation, the user interface may present a visual indicator (indicator) in a presentation area on a display device. For example, the visual indicator may comprise a circle, icon, picture, animation, and so forth. The position of the indicator in the presentation area may be based at least in part on the coordinates with respect to the emotional space. Continuing the earlier example, the coordinates of the indicator in the presentation area may be based on the coordinates in the emotional space as indicated by the sentiment data.

A characteristic of the indicator at a given time may be determined based on what region the indicator is associated with. For example, if the coordinates in the emotional space are within the boundary of a region that has a specified characteristic of "blue", then the presentation of the indicator in the presentation area of the user interface may involve the indicator being colored "blue". As the sentiment data changes over time, the indicator may move around the presentation area, and the corresponding characteristic of the indicator would change accordingly. Continuing the example, the indicator may be associated with a second region that is associated with the color "orange", and the user interface presents the indicator with that color.

As described above, the sentiment data may include labels that are indicative of an emotional state. A descriptor library may be used to determine descriptors that are associated with those labels. Once determined, the descriptors may be presented in the user interface. For example, the label may have a value of "anxious" which his associated with descriptors "antsy", "edgy", "perturbed", and so forth. During presentation, one of these descriptors may be selected and presented in the user interface near the indicator. In some implementations the descriptors may be selected at random. In the event that the sentiment data over time maintains the same label, indicators in the user interface would be presented with changing descriptors. This presentation of changing descriptors provides a more dynamic and engaging user interface for the user. Descriptors may be presented using visual effects, such as fading. For example, a descriptor may fade in over some length of time for presentation in the user interface and then fade out after another length of time.

The user may not be speaking continuously. For example, the user may pause, allow someone else to speak, and so forth. If speech from the user is not detected, and no updated sentiment data has been available for some threshold amount of time, one or more characteristics of the indicator may be changed to indicate an idle condition. For example, the color of the indicator may be changed to white, the indicator may present an animated pulsation effect in which the size of the indicator on the display device increases and decreases over time, the indicator may be presented with a blur effect around the perimeter of the indicator, and so forth. When the system determines that new sentiment data is available, the user interface may be updated to present as described above.

Other information may be presented in the user interface. For example, a historical trail may be presented in the presentation area of the user interface that is indicative of previous locations of the indicator in the presentation area for some previous window of time. This facilitates the user seeing how their emotional state has changed over some period of time.

The user interface may also provide transcribed text associated with the sentiment data, such as transcription data as from an automated speech recognition (ASR) system. The presentation of the transcribed text may help the user better associate the emotional information provided in the user interface with a particular portion of their speech.

The system may also provide information to more than one enrolled user. For example, sentiment data for two different users may be determined and presented in the user interface. To facilitate the distinction as to which indicator is associated with a particular user, indicators associated with different users may have different shapes, name labels may be presented, and so forth.

The user interface provides simplified, accessible, and easy to comprehend information to the user about the sentiment data indicative of their emotional state as expressed in their speech. The user may use the information presented to adjust their behavior and improve their interactions with others.

Illustrative System

FIG. 1 is an illustrative system 100 that processes speech of a user to determine sentiment data that is indicative of an emotional state as conveyed by the speech and presenting output related to that sentiment data, according to one implementation.

The user 102 may have one or more wearable devices 104 on or about their person. The wearable device 104 may be implemented in various physical form factors including, but not limited to, the following: hats, headbands, necklaces, pendants, brooches, torcs, armlets, brassards, bracelets, wristbands, and so forth. In this illustration, the wearable device 104 is depicted as a wristband.

The wearable device 104 may use a communication link 106 to maintain communication with a computing device 108. For example, the computing device 108 may include a phone, tablet computer, personal computer, server, internet enabled device, voice activated device, smart-home device, and so forth. The communication link 106 may implement at least a portion of the Bluetooth Low Energy specification.

The wearable device 104 includes a housing 110. The housing 110 comprises one or more structures that support a microphone array 112. For example, the microphone array 112 may comprise two or more microphones arranged to acquire sound from ports at different locations through the housing 110. As described below, a microphone pattern 114 may provide gain or directivity using a beamforming algorithm. Speech 116 by the user 102 or other sources within range of the microphone array 112 may be detected by the microphone array 112 and raw audio data 118 may be acquired. In other implementations raw audio data 118 may be acquired from other devices.

A voice activity detector module 120 may be used to process the raw audio data 118 and determine if speech 116 is present. For example, the microphone array 112 may obtain raw audio data 118 that contains ambient noises such as traffic, wind, and so forth. Raw audio data 118 that is not deemed to contain speech 116 may discarded. Resource consumption is minimized by discarding raw audio data 118 that does not contain speech 116. For example, power consumption, demands for memory and computational resources, communication bandwidth, and so forth are minimized by limiting further processing of raw audio data 118 determined to not likely contain speech 116.

The voice activity detector module 120 may use one or more techniques to determine voice activity. For example, characteristics of the signals present in the raw audio data 118 such as frequency, energy, zero-crossing rate, and so forth may be analyzed with respect to threshold values to determine characteristics that are deemed likely to be human speech.

Once at least a portion of the raw audio data 118 has been determined to contain speech 116, an audio preprocessing module 122 may further process this portion to determine first audio data 124. In some implementations, the audio preprocessing module 122 may apply one or more of a beamforming algorithm, noise reduction algorithms, filters, and so forth to determine the first audio data 124. For example, the audio preprocessing module 122 may use a beamforming algorithm to provide directivity or gain and improve the signal to noise ratio (SNR) of the speech 116 from the user 102 with respect to speech 116 or noise from other sources.

The wearable device 104 may include one or more sensors 126 that generate sensor data 128. For example, the sensors 126 may include accelerometers, pulse oximeters, and so forth. The sensors 126 are discussed in more detail with regard to FIG. 2.

The audio preprocessing module 122 may use information from one or more sensors 126 during operation. For example, sensor data 128 from an accelerometer may be used to determine orientation of the wearable device 104. Based on the orientation, the beamforming algorithm may be operated to provide a microphone pattern 114 that includes a location where the user's 102 head is expected to be.

A data transfer module 130 may use a communication interface 132 to send the first audio data 124, sensor data 128, or other data to the computing device 108 using the communication link 106. For example, the data transfer module 130 may determine that a memory within the wearable device 104 has reached a predetermined quantity of stored first audio data 124. The communication interface 132 may comprise a Bluetooth Low Energy device that is operated responsive to commands from the data transfer module 130 to send the stored first audio data 124 to the computing device 108.

In some implementations, the first audio data 124 may be encrypted prior to transmission over the communication link 106. The encryption may be performed prior to storage in the memory of the wearable device 104, prior to transmission via the communication link 106, or both.

Communication between the wearable device 104 and the computing device 108 may be persistent or intermittent. For example, the wearable device 104 may determine and store first audio data 124 even while the communication link 106 to the computing device 108 is unavailable. At a later time, when the communication link 106 is available, the first audio data 124 may be sent to the computing device 108.

The wearable device 104 may include one or more output devices 134. For example, the output devices 134 may include a light emitting diode, haptic output device, speaker, and so forth. The output devices 134 are described in more detail with regard to FIG. 2.

The computing device 108 may include a communication interface 132. For example, the communication interface 132 of the computing device 108 may comprise a Bluetooth Low Energy device, a WiFi network interface device, and so forth. The computing device 108 receives the first audio data 124 from the wearable device 104 via the communication link 106.

The computing device 108 may use a turn detection module 136 to determine that portions of the first audio data 124 are associated with different speakers. As described in more detail below with regard to FIG. 4, when more than one person is speaking a "turn" is a contiguous portion of speech by a single person. For example, a first turn may include several sentences spoken by a first person, while a second turn includes a response by the second person. The turn detection module 136 may use one or more characteristics in the first audio data 124 to determine that a turn has taken place. For example, a turn may be detected based on a pause in speech 116, change in pitch, change in signal amplitude, and so forth. Continuing the example, if the pause between words exceeds 350 milliseconds, data indicative of a turn may be determined.

In one implementation, the turn detection module 136 may process segments of the first audio data 124 to determine if the person speaking at the beginning of the segment is the same as the person speaking at the end. The first audio data 124 may be divided into segments and subsegments. For example, each segment may be six seconds long with a first subsegment that includes a beginning two seconds of the segment and a second subsegment that includes the last two seconds of the segment. The data in the first subsegment is processed to determine a first set of features and the data in the second subsegment is processed to determine a second set of features. Segments may overlap, such that at least some data is duplicated between successive segments. If the first set of features and the second set of features are determined to be within a threshold value of one another, they may be deemed to have been spoken by the same person. If the first set of features and the second set of features are not within the threshold value of one another, they may be deemed to have been spoken by different people. A segment that includes speech from two different people may be designated as a break between one speaker and another. In this implementation, those breaks between speakers may be used to determine the boundaries of a turn. For example, a turn may be determined to begin and end when a segment includes speech from two different people.

In some implementations, the turn detection module 136 may operate in conjunction with, or as part of, a speech identification module 138, as described below. For example, if the speech identification module 138 identifies that a first segment is spoken by a first user 102 and a second segment is spoken by a second user 102, data indicative of a turn may be determined.

The speech identification module 138 may access user profile data 140 to determine if the first audio data 124 is associated with the user 102. For example, user profile data 140 may comprise information about speech 116 provided by the user 102 during an enrollment process. During enrollment, the user 102 may provide a sample of their speech 116 which is then processed to determine features that may be used to identify if speech 116 is likely to be from that user 102.

The speech identification module 138 may process at least a portion of the first audio data 124 that is designated as a particular turn to determine if the user 102 is the speaker. For example, the first audio data 124 of the first turn may be processed by the speech identification module 138 to determine a confidence level of 0.97 that the first turn is the user 102 speaking. A threshold confidence value of 0.95 may be specified. Continuing the example, the first audio data 124 of the second turn may be processed by the speech identification module 138 that determines a confidence level of 0.17 that the second turn is the user 102 speaking.

Second audio data 142 is determined that comprises the portion(s) of the first audio data 124 that is determined to be speech 116 from the user 102. For example, the second audio data 142 may consist of the speech 116 which exhibits a confidence level greater than the threshold confidence value of 0.95. As a result, the second audio data 142 omits speech 116 from other sources, such as someone who is in conversation with the user 102.

An audio feature module 144 uses the second audio data 142 to determine audio feature data 146. For example, the audio feature module 144 may use one or more systems such as signal analysis, classifiers, neural networks, and so forth to generate the audio feature data 146. The audio feature data 146 may comprise values, vectors, and so forth. For example, the audio feature module 144 may use a convolutional neural network that accepts as input the second audio data 142 and provides as output vectors in a vector space. The audio feature data 146 may be representative of features such as rising pitch over time, speech cadence, energy intensity per phoneme, duration of a turn, and so forth.

A feature analysis module 148 uses the audio feature data 146 to determine sentiment data 150. Human speech involves a complex interplay of biological systems on the part of the person speaking. These biological systems are affected by the physical and emotional state of the person. As a result, the speech 116 of the user 102 may exhibit changes. For example, a person who is calm sounds different from a person who is excited. This may be described as "emotional prosody" and is separate from the meaning of the words used. For example, in some implementations the feature analysis module 148 may use the audio feature data 146 to assess emotional prosody without assessment of the actual content of the words used.

The feature analysis module 148 determines the sentiment data 150 that is indicative of a possible emotional state of the user 102 based on the audio feature data 146. The feature analysis module 148 may determine various values that are deemed to be representative of emotional state. In some implementations these values may be representative of emotional primitives. (See Kehrein, Roland. (2002). The prosody of authentic emotions. 27. 10.1055/s-2003-40251.) For example, the emotional primitives may include valence, activation, and dominance. A valence value may be determined that is representative of a particular change in pitch of the user's voice over time. Certain valence values indicative of particular changes in pitch may be associated with certain emotional states. An activation value may be determined that is representative of pace of the user's speech over time. As with valence values, certain activation values may be associated with certain emotional states. A dominance value may be determined that is representative of rise and fall patterns of the pitch of the user's voice overtime. As with valence values, certain dominance values may be associated with certain emotional states. Different values of valence, activation, and dominance may correspond to particular emotions. (See Grimm, Michael (2007). Primitives-based evaluation and estimation of emotions in speech. Speech Communication 49 (2007) 787-800.)

Other techniques may be used by the feature analysis module 148. For example, the feature analysis module 148 may determine Mel Frequency Cepstral Coefficients (MFCC) of at least a portion of the second audio data 142. The MFCC may then be used to determine an emotional class associated with the portion. The emotional class may include one or more of angry, happy, sad, or neutral. (See Rozgic, Viktor, et. al, (2012). Emotion Recognition using Acoustic and Lexical Features. 13th Annual Conference of the International Speech Communication Association 2012, INTERSPEECH 2012. 1.)

In other implementations the feature analysis module 148 may include analysis of the words spoken and their meaning. For example, an automated speech recognition (ASR) system may be used to determine the text of the words spoken. This information may then be used to determine the sentiment data 150. For example, presence in the second audio data 142 of words that are associated with a positive connotation, such as compliments or praise, may be used to determine the sentiment data 150. In another example, word stems may be associated with particular sentiment categories. The word stems may be determined using ASR, and the particular sentiment categorizes determined. (See Rozgic, Viktor, et. al, (2012). Emotion Recognition using Acoustic and Lexical Features. 13th Annual Conference of the International Speech Communication Association 2012, INTERSPEECH 2012. 1.) Other techniques may be used determine emotional state based at least in part on the meaning of words spoken by the user 102.

The sentiment data 150 determined by the feature analysis module 148 may be expressed as one or more numeric values, vectors, words, and so forth. For example, the sentiment data 150 may comprise one or more vectors in an n-dimensional space. In another example, the sentiment data 150 may comprise associated labels. For example, a machine learning system may be trained to associate particular feature data with particular labels indicative of emotional state. In another example, the labels may be determined by particular combinations of other values, such as valence, activation, and dominance values. The sentiment data 150 may comprise values that are non-normative. For example, a sentiment value that is expressed as a negative number may not be representative of an emotion that is considered to be bad.

The computing device 108 may include a sensor data analysis module 152. The sensor data analysis module 152 may process the sensor data 128 and generate user status data 154. For example, the sensor data 128 obtained from sensors 126 on the wearable device 104 may comprise information about movement obtained from an accelerometer, pulse rates obtained from a pulse oximeter, and so forth. The user status data 154 may comprise information such as total movement by the wearable device 104 during particular time intervals, pulse rates during particular time intervals, and so forth. The user status data 154 may provide information that is representative of the physiological state of the user 102.

In some implementations the sentiment data 150 may be determined based at least in part on the user status data 154. For example, information about the pulse rate at a given time of the user 102 with respect to their normal baseline pulse rate may be used as an input in conjunction with the audio feature data 146 to the feature analysis module 148.

A presentation module 156 may use one or more of a region library 158, descriptor library 160, or other information to determine output data 162. As described above, the sentiment data 150 may be indicative of values associated with one or more dimensions, such as an activation value, valence value, dominance value, and one or more labels. The region library 158 associates particular regions within an emotional space described by one or more emotional dimensions with one or more specified characteristics. For example, a particular region within the emotional space may be associated with a particular color. Regions are described in more detail with regard to FIG. 7.

The descriptor library 160 associates a label with one or more descriptors. As descried above, the feature analysis module 148 or another system may provide sentiment data 150 that indicates one or more labels. These labels may be indicative of an emotional state. For example, the sentiment data 150 may indicate a label of "bored". The descriptor library 160 provides an association between a label and one or more descriptors. For example, the descriptors may comprise words that are deemed synonymous or equivalent to the emotional state described by the label. Continuing the example, the label of "bored" may be associated with descriptors such as "uninterested", "disinterested", "jaded", and so forth. The descriptor library 160 is discussed in more detail with regard to FIG. 6.

The computing device 108 may generate output data 162 based on the sentiment data 150. For example, the output data 162 may comprise hypertext markup language (HTML) instructions that, when processed by a browser engine, generate an image of a graphical user interface (GUI). The output data 162 may then be used to operate one or more output devices 134. Continuing the examples, the GUI may be presented on a display device, to provide output 164. The output 164 may include a user interface 166, such as the GUI depicted here with one or more interface elements 168. Some implementations of the user interface 166 are discussed in more detail with regard to FIGS. 8-13.

The system may provide output 164 based on data obtained over various time intervals. For example, the sentiment data 150 may be presented on a real time or near-real time basis using raw audio data 118 obtained in the last n seconds where n is greater than zero, for a last turn or transition in the conversation from the user 102 to another person, and so forth.

It is understood that the various functions, modules, and operations described in this system 100 may be performed by various combinations of devices. For example, the system 100 may operate entirely on a computing device 108 such as a smartphone.

Figure 2:
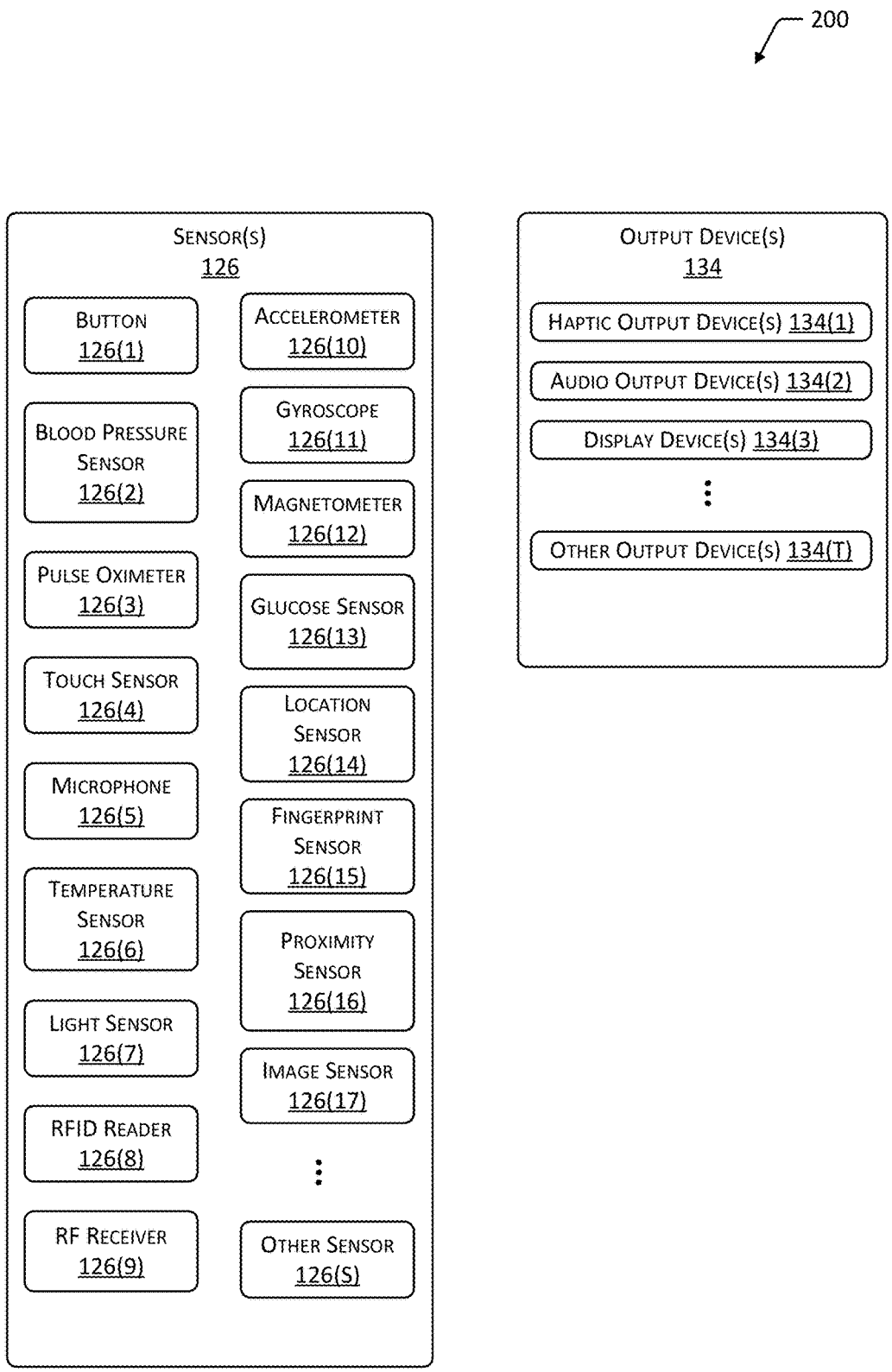
FIG. 2 illustrates a block diagram of sensors and output devices that may be used during operation of the system, according to one implementation.

FIG. 2 illustrates a block diagram 200 of sensors 126 and output devices 134 that may be used by the wearable device 104, the computing device 108, or other devices during operation of the system 100, according to one implementation. As described above with regard to FIG. 1, the sensors 126 may generate sensor data 128.

The one or more sensors 126 may be integrated with or internal to a computing device, such as the wearable device 104, the computing device 108, and so forth. For example, the sensors 126 may be built-in to the wearable device 104 during manufacture. In other implementations, the sensors 126 may be part of another device. For example, the sensors 126 may comprise a device external to, but in communication with, the computing device 108 using Bluetooth, Wi-Fi, 3G, 4G, LTE, ZigBee, Z-Wave, or another wireless or wired communication technology.

The one or more sensors 126 may include one or more buttons 126(1) that are configured to accept input from the user 102. The buttons 126(1) may comprise mechanical, capacitive, optical, or other mechanisms. For example, the buttons 126(1) may comprise mechanical switches configured to accept an applied force from a touch of the user 102 to generate an input signal. In some implementations input from one or more sensors 126 may be used to initiate acquisition of the raw audio data 118. For example, activation of a button 126(1) may initiate acquisition of the raw audio data 118.

A blood pressure sensor 126(2) may be configured to provide sensor data 128 that is indicative of the user's 102 blood pressure. For example, the blood pressure sensor 126(2) may comprise a camera that acquires images of blood vessels and determines the blood pressure by analyzing the changes in diameter of the blood vessels over time. In another example, the blood pressure sensor 126(2) may comprise a sensor transducer that is in contact with the skin of the user 102 that is proximate to a blood vessel.

A pulse oximeter 126(3) may be configured to provide sensor data 128 that is indicative of a cardiac pulse rate and data indicative of oxygen saturation of the user's 102 blood. For example, the pulse oximeter 126(3) may use one or more light emitting diodes (LEDs) and corresponding detectors to determine changes in apparent color of the blood of the user 102 resulting from oxygen binding with hemoglobin in the blood, providing information about oxygen saturation. Changes over time in apparent reflectance of light emitted by the LEDs may be used to determine cardiac pulse.

The sensors 126 may include one or more touch sensors 126(4). The touch sensors 126(4) may use resistive, capacitive, surface capacitance, projected capacitance, mutual capacitance, optical, Interpolating Force-Sensitive Resistance (IFSR), or other mechanisms to determine the position of a touch or near-touch of the user 102. For example, the IFSR may comprise a material configured to change electrical resistance responsive to an applied force. The location within the material of that change in electrical resistance may indicate the position of the touch.

One or more microphones 126(5) may be configured to acquire information about sound present in the environment. In some implementations, a plurality of microphones 126(5)

may be used to form the microphone array 112. As described above, the microphone array 112 may implement beamforming techniques to provide for directionality of gain.

A temperature sensor (or thermometer) 126(6) may provide information indicative of a temperature of an object. The temperature sensor 126(6) in the computing device may be configured to measure ambient air temperature proximate to the user 102, the body temperature of the user 102, and so forth. The temperature sensor 126(6) may comprise a silicon bandgap temperature sensor, thermistor, thermocouple, or other device. In some implementations, the temperature sensor 126(6) may comprise an infrared detector configured to determine temperature using thermal radiation.

The sensors 126 may include one or more light sensors 126(7). The light sensors 126(7) may be configured to provide information associated with ambient lighting conditions such as a level of illumination. The light sensors 126(7) may be sensitive to wavelengths including, but not limited to, infrared, visible, or ultraviolet light. In contrast to a camera, the light sensor 126(7) may typically provide a sequence of amplitude (magnitude) samples and color data while the camera provides a sequence of two-dimensional frames of samples (pixels).

One or more radio frequency identification (RFID) readers 126(8), near field communication (NFC) systems, and so forth, may also be included as sensors 126. The user 102, objects around the computing device, locations within a building, and so forth, may be equipped with one or more radio frequency (RF) tags. The RF tags are configured to emit an RF signal. In one implementation, the RF tag may be an RFID tag configured to emit the RF signal upon activation by an external signal. For example, the external signal may comprise an RF signal or a magnetic field configured to energize or activate the RFID tag. In another implementation, the RF tag may comprise a transmitter and a power source configured to power the transmitter. For example, the RF tag may comprise a Bluetooth Low Energy (BLE) transmitter and battery. In other implementations, the tag may use other techniques to indicate its presence. For example, an acoustic tag may be configured to generate an ultrasonic signal, which is detected by corresponding acoustic receivers. In yet another implementation, the tag may be configured to emit an optical signal.

One or more RF receivers 126(9) may also be included as sensors 126. In some implementations, the RF receivers 126(9) may be part of transceiver assemblies. The RF receivers 126(9) may be configured to acquire RF signals associated with Wi-Fi, Bluetooth, ZigBee, Z-Wave, 3G, 4G, LTE, or other wireless data transmission technologies. The RF receivers 126(9) may provide information associated with data transmitted via radio frequencies, signal strength of RF signals, and so forth. For example, information from the RF receivers 126(9) may be used to facilitate determination of a location of the computing device, and so forth.

The sensors 126 may include one or more accelerometers 126(10). The accelerometers 126(10) may provide information such as the direction and magnitude of an imposed acceleration, tilt relative to local vertical, and so forth. Data such as rate of acceleration, determination of changes in direction, speed, tilt, and so forth, may be determined using the accelerometers 126(10).

A gyroscope 126(11) provides information indicative of rotation of an object affixed thereto. For example, the gyroscope 126(11) may indicate whether the device has been rotated.

A magnetometer 126(12) may be used to determine an orientation by measuring ambient magnetic fields, such as the terrestrial magnetic field. For example, output from the magnetometer 126(12) may be used to determine whether the device containing the sensor 126, such as the computing device 108, has changed orientation or otherwise moved. In other implementations, the magnetometer 126(12) may be configured to detect magnetic fields generated by another device.

A glucose sensor 126(13) may be used to determine a concentration of glucose within the blood or tissues of the user 102. For example, the glucose sensor 126(13) may comprise a near infrared spectroscope that determines a concentration of glucose or glucose metabolites in tissues. In another example, the glucose sensor 126(13) may comprise a chemical detector that measures presence of glucose or glucose metabolites at the surface of the user's skin.

A location sensor 126(14) is configured to provide information indicative of a location. The location may be relative or absolute. For example, a relative location may indicate "kitchen", "bedroom", "conference room", and so forth. In comparison, an absolute location is expressed relative to a reference point or datum, such as a street address, geolocation comprising coordinates indicative of latitude and longitude, grid square, and so forth. The location sensor 126(14) may include, but is not limited to, radio navigation-based systems such as terrestrial or satellite-based navigational systems. The satellite-based navigation system may include one or more of a Global Positioning System (GPS) receiver, a Global Navigation Satellite System (GLONASS) receiver, a Galileo receiver, a BeiDou Navigation Satellite System (BDS) receiver, an Indian Regional Navigational Satellite System, and so forth. In some implementations, the location sensor 126(14) may be omitted or operate in conjunction with an external resource such as a cellular network operator providing location information, or Bluetooth beacons.

A fingerprint sensor 126(15) is configured to acquire fingerprint data. The fingerprint sensor 126(15) may use an optical, ultrasonic, capacitive, resistive, or other detector to obtain an image or other representation of features of a fingerprint. For example, the fingerprint sensor 126(15) may comprise a capacitive sensor configured to generate an image of the fingerprint of the user 102.

A proximity sensor 126(16) may be configured to provide sensor data 128 indicative of one or more of a presence or absence of an object, a distance to the object, or characteristics of the object. The proximity sensor 126(16) may use optical, electrical, ultrasonic, electromagnetic, or other techniques to determine a presence of an object. For example, the proximity sensor 126(16) may comprise a capacitive proximity sensor configured to provide an electrical field and determine a change in electrical capacitance due to presence or absence of an object within the electrical field.

An image sensor 126(17) comprises an imaging element to acquire images in visible light, infrared, ultraviolet, and so forth. For example, the image sensor 126(17) may comprise a complementary metal oxide (CMOS) imaging element or a charge coupled device (CCD).

The sensors 126 may include other sensors 126(S) as well. For example, the other sensors 126(S) may include strain gauges, anti-tamper indicators, and so forth. For example, strain gauges or strain sensors may be embedded within the wearable device 104 and may be configured to provide information indicating that at least a portion of the wearable device 104 has been stretched or displaced such that the wearable device 104 may have been donned or doffed.

In some implementations, the sensors 126 may include hardware processors, memory, and other elements configured to perform various functions. Furthermore, the sensors 126 may be configured to communicate by way of a network or may couple directly with the other devices.

The computing device may include or may couple to one or more output devices 134. The output devices 134 are configured to generate signals which may be perceived by the user 102, detectable by the sensors 126, or a combination thereof.

Haptic output devices 134(1) are configured to provide a signal, which results in a tactile sensation to the user 102. The haptic output devices 134(1) may use one or more mechanisms such as electrical stimulation or mechanical displacement of a mass to provide the signal. For example, the haptic output devices 134(1) may be configured to generate a modulated electrical signal, which produces an apparent tactile sensation in one or more fingers of the user 102. In another example, the haptic output devices 134(1) may comprise piezoelectric or rotary motor devices configured to provide a vibration that may be felt by the user 102.

One or more audio output devices 134(2) are configured to provide acoustic output. The acoustic output includes one or more of infrasonic sound, audible sound, or ultrasonic sound. The audio output devices 134(2) may use one or more mechanisms to generate the acoustic output. These mechanisms may include, but are not limited to, the following: voice coils, piezoelectric elements, magnetostrictive elements, electrostatic elements, and so forth. For example, a piezoelectric buzzer or a speaker may be used to provide acoustic output by an audio output device 134(2).

The display devices 132(3) may be configured to provide output that may be seen by the user 102 or detected by a light-sensitive detector such as the image sensor 126(17) or light sensor 126(7). The output may be monochrome or color. The display devices 132(3) may be emissive, reflective, or both. An emissive display device 132(3), such as using LEDs, is configured to emit light during operation. In comparison, a reflective display device 132(3), such as using an electrophoretic element, relies on ambient light to present an image. Backlights or front lights may be used to illuminate non-emissive display devices 132(3) to provide visibility of the output in conditions where the ambient light levels are low.

The display mechanisms of display devices 132(3) may include, but are not limited to, micro-electromechanical systems (MEMS), spatial light modulators, electroluminescent displays, quantum dot displays, liquid crystal on silicon (LCOS) displays, cholesteric displays, interferometric displays, liquid crystal displays, electrophoretic displays, LED displays, and so forth. These display mechanisms are configured to emit light, modulate incident light emitted from another source, or both. The display devices 132(3) may operate as panels, projectors, and so forth.

The display devices 132(3) may be configured to present images. For example, the display devices 132(3) may comprise a pixel-addressable display. The image may comprise at least a two-dimensional array of pixels or a vector representation of an at least two-dimensional image.

In some implementations, the display devices 132(3) may be configured to provide non-image data, such as text or numeric characters, colors, and so forth. For example, a segmented electrophoretic display device 132(3), segmented LED, and so forth, may be used to present information such as letters or numbers. The display devices 132(3) may also be configurable to vary the color of the segment, such as using multicolor LED segments.

Other output devices 134(T) may also be present. For example, the other output devices 134(T) may include scent dispensers.

Figure 3:
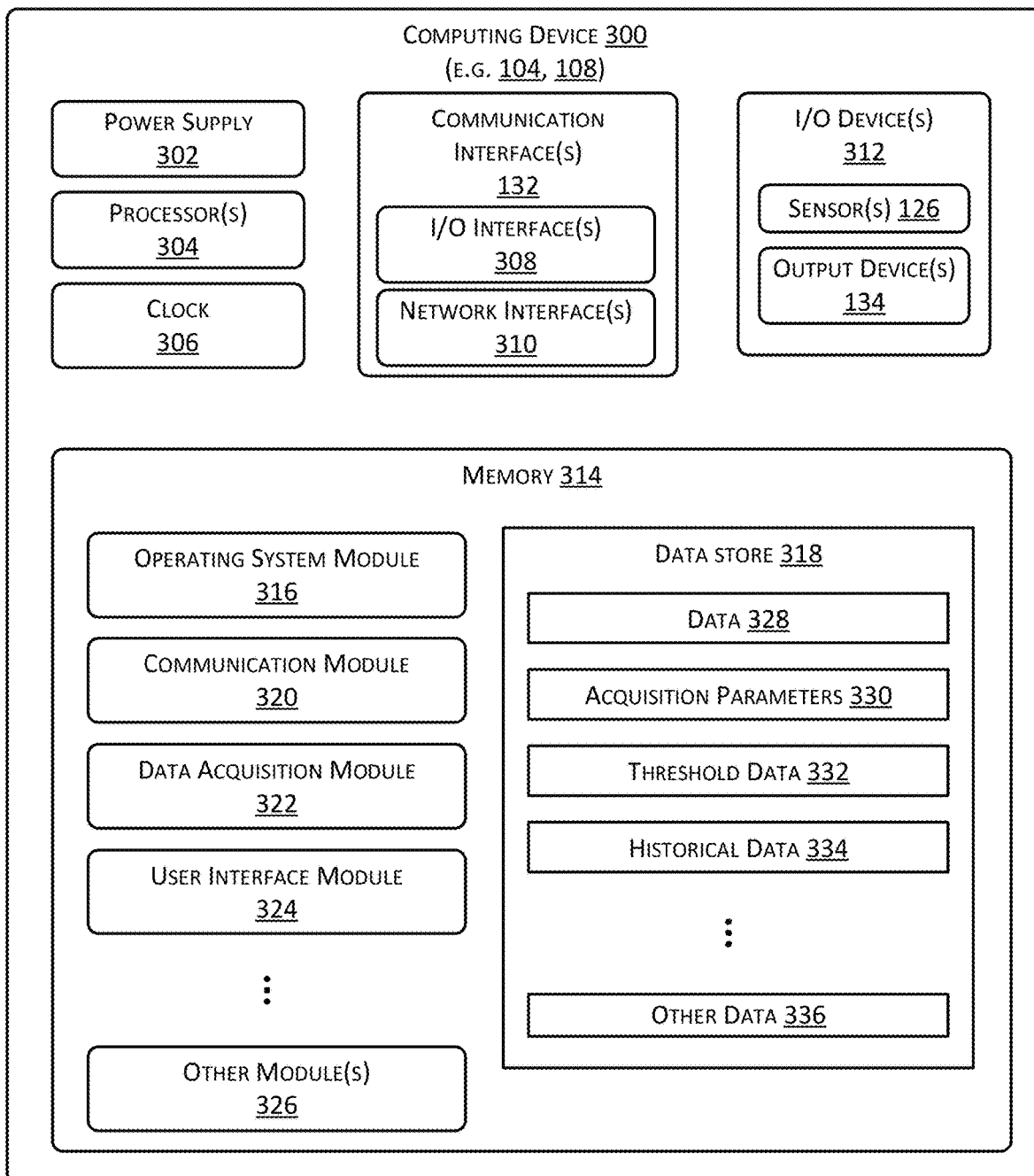
FIG. 3 illustrates a block diagram of a computing device(s) such as a wearable device, smartphone, or other devices, according to one implementation.

FIG. 3 illustrates a block diagram of a computing device 300 configured to support operation of the system 100. As described above, the computing device 300 may be the wearable device 104, the computing device 108, and so forth.

One or more power supplies 302 are configured to provide electrical power suitable for operating the components in the computing device 300. In some implementations, the power supply 302 may comprise a rechargeable battery, fuel cell, photovoltaic cell, power conditioning circuitry, wireless power receiver, and so forth.

The computing device 300 may include one or more hardware processors 304 (processors) configured to execute one or more stored instructions. The processors 304 may comprise one or more cores. One or more clocks 306 may provide information indicative of date, time, ticks, and so forth. For example, the processor 304 may use data from the clock 306 to generate a timestamp, trigger a preprogrammed action, and so forth.

The computing device 300 may include one or more communication interfaces 132 such as input/output (I/O) interfaces 308, network interfaces 310, and so forth. The communication interfaces 132 enable the computing device 300, or components thereof, to communicate with other devices or components. The communication interfaces 132 may include one or more I/O interfaces 308. The I/O interfaces 308 may comprise interfaces such as Inter-Integrated Circuit (I2C), Serial Peripheral Interface bus (SPI), Universal Serial Bus (USB) as promulgated by the USB Implementers Forum, RS-232, and so forth.

The I/O interface(s) 308 may couple to one or more I/O devices 312. The I/O devices 312 may include input devices such as one or more of the sensors 126. The I/O devices 312 may also include output devices 134 such as one or more of an audio output device 134(2), a display device 134(3), and so forth. In some embodiments, the I/O devices 312 may be physically incorporated with the computing device 300 or may be externally placed.

The network interfaces 310 are configured to provide communications between the computing device 300 and other devices, such as the sensors 126, routers, access devices, and so forth. The network interfaces 310 may include devices configured to couple to wired or wireless personal area networks (PANs), local area networks (LANs), wide area networks (WANs), and so forth. For example, the network interfaces 310 may include devices compatible with Ethernet, Wi-Fi, Bluetooth, ZigBee, 4G, 5G, LTE, and so forth.

The computing device 300 may also include one or more buses or other internal communications hardware or software that allow for the transfer of data between the various modules and components of the computing device 300.

As shown in FIG. 3, the computing device 300 includes one or more memories 314. The memory 314 comprises one or more computer-readable storage media (CRSM). The CRSM may be any one or more of an electronic storage medium, a magnetic storage medium, an optical storage medium, a quantum storage medium, a mechanical computer storage medium, and so forth. The memory 314 provides storage of computer-readable instructions, data structures, program modules, and other data for the operation of the computing device 300. A few example functional modules are shown stored in the memory 314, although the same functionality may alternatively be implemented in hardware, firmware, or as a system on a chip (SOC).

The memory 314 may include at least one operating system (OS) module 316. The OS module 316 is configured to manage hardware resource devices such as the I/O interfaces 308, the network interfaces 310, the I/O devices 312, and provide various services to applications or modules executing on the processors 304. The OS module 316 may implement a variant of the FreeBSD operating system as promulgated by the FreeBSD Project; other UNIX or UNIX-like operating system; a variation of the Linux operating system as promulgated by Linus Torvalds; the Windows operating system from Microsoft Corporation of Redmond, Wash., USA; the Android operating system from Google Corporation of Mountain View, Calif., USA; the iOS operating system from Apple Corporation of Cupertino, Calif., USA; or other operating systems.

Also stored in the memory 314 may be a data store 318 and one or more of the following modules. These modules may be executed as foreground applications, background tasks, daemons, and so forth. The data store 318 may use a flat file, database, linked list, tree, executable code, script, or other data structure to store information. In some implementations, the data store 318 or a portion of the data store 318 may be distributed across one or more other devices including the computing devices 300, network attached storage devices, and so forth.

A communication module 320 may be configured to establish communications with one or more of other computing devices 300, the sensors 126, and so forth. The communications may be authenticated, encrypted, and so forth. The communication module 320 may also control the communication interfaces 132.

The memory 314 may also store a data acquisition module 322. The data acquisition module 322 is configured to acquire raw audio data 118, sensor data 126, and so forth. In some implementations, the data acquisition module 322 may be configured to operate the one or more sensors 126, the microphone array 112, and so forth. For example, the data acquisition module 322 may determine that the sensor data 128 satisfies a trigger event. The trigger event may comprise values of sensor data 128 for one or more sensors 126 exceeding a threshold value. For example, if a pulse oximeter 126(3) on the wearable device 104 indicates that the pulse of the user 102 has exceeded a threshold value, the microphone array 112 may be operated to generate raw audio data 118.

In another example, the data acquisition module 322 on the wearable device 104 may receive instructions from the computing device 108 to obtain raw audio data 118 at a specified interval, at a scheduled time, and so forth. For example, the computing device 108 may send instructions to acquire raw audio data 118 for 60 seconds every 540 seconds. The raw audio data 118 may then be processed with the voice activity detector module 120 to determine if speech 116 is present. If speech 116 is detected, the first audio data 124 may be obtained and then sent to the computing device 108.

In yet another example, the data acquisition module 322 may obtain raw audio data 118 responsive to a command by the user 102. For example, the user 102 may activate a control in the user interface 166 to begin operation of the system.

A user interface module 324 provides a user interface 166 using one or more of the I/O devices 312. The user interface module 324 may be used to obtain input from the user 102, present information to the user 102, and so forth. For example, the user interface module 324 may present a graphical user interface on the display device 134(3) and accept user input using the touch sensor 126(4).

One or more other modules 326, such as the voice activity detector module 120, the audio preprocessing module 122, the data transfer module 130, the turn detection module 136, the speech identification module 138, the audio feature module 144, the feature analysis module 148, the sensor data analysis module 152, the presentation module 156, and so forth may also be stored in the memory 314.

Data 328 may be stored in the data store 318. For example, the data 328 may comprise one or more of raw audio data 118, first audio data 124, sensor data 128, user profile data 140, second audio data 142, sentiment data 150, user status data 154, output data 162, and so forth.

One or more acquisition parameters 330 may be stored in the memory 314. The acquisition parameters 330 may comprise parameters such as audio sample rate, audio sample frequency, audio frame size, and so forth.

Threshold data 332 may be stored in the memory 314. For example, the threshold data 332 may specify one or more thresholds used by the voice activity detector module 120 to determine if the raw audio data 118 includes speech 116.

The computing device 300 may maintain historical data 334. The historical data 334 may be used to provide information about trends or changes over time. For example, the historical data 334 may comprise previously determined sentiment data 150. In another example, the historical data 334 may comprise user status data 154.

Other data 336 may also be stored in the data store 318.

In different implementations, different computing devices 300 may have different capabilities or capacities. For example, the computing device 108 may have significantly more processor 304 capability and memory 314 capacity compared to the wearable device 104. In one implementation, the wearable device 104 may determine the first audio data 124 and send the first audio data 124 to the computing device 108. In another implementation, the wearable device 104 may generate the sentiment data 150 and present the output 164 as a user interface 166 presented on a display device of the wearable device 104. Other combinations of distribution of data processing and functionality may be used in other implementations.

Figure 4:
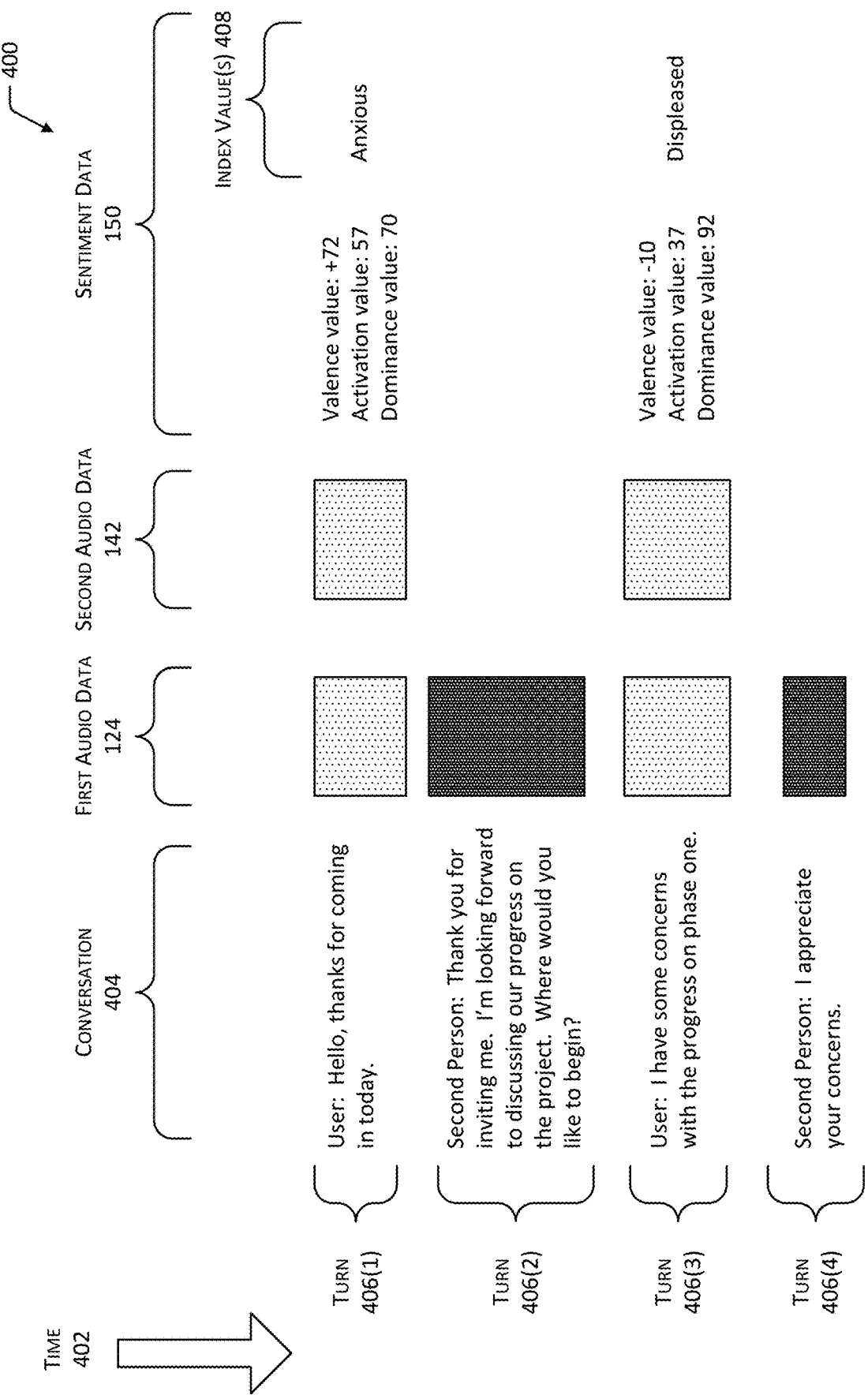
FIG. 4 illustrates parts of a conversation between a user and a second person, according to one implementation.

FIG. 4 illustrates at 400 parts of a conversation between the user 102 and a second person, according to one implementation. In this figure, time 402 increases down the page. A conversation 404 may comprise speech 116 produced by one or more people. For example, as shown here the user 102 may be talking with a second person. In another implementation, the conversation 404 may comprise speech 116 from the user 102 speaking to themselves. Several turns 406(1)-(4) of the conversation 404 are illustrated here. For example, a turn 406 may comprise a contiguous portion of speech 116 by a single person. In this example, the first turn 406(1) is the user 102 saying "Hello, thanks for coming in today." while the second turn 406(2) is the second person responding with "Thank you for inviting me. I'm looking forward to . . . ". The first turn 406(1) is a single sentence while the second turn 406(2) is several sentences.

The system 100 acquires the raw audio data 118 that is the used to determine the first audio data 124. The first audio data 124 is illustrated here as blocks, with different shading to indicate the respective speaker. For example, a block may be representative of a particular period of time, set of one or more frames of audio data, and so forth.

The turn detection module 136 may be used to determine the boundaries of each turn 406. For example, the turn detection module 136 may determine a turn 406 based on a change in the sound of who is speaking, on the basis of time, and so forth.

The speech identification module 138 is used to determine whether the portion of the first audio data 124, such as a particular turn 406, is speech 116 from the user 102. In determining the second audio data 142, the audio for turns 406 that are not associated with the user 102 are omitted. As a result, the second audio data 142 may consist of audio data that is deemed to represent speech 116 from the user 102. The system 100 is thus prevented from processing speech 116 of the second person.

The second audio data 142 is processed and the sentiment data 150 is determined. The sentiment data 150 may be determined for various portions of the second audio data 142. For example, the sentiment data 150 may be determined for a particular turn 406 as illustrated here. In another example, the sentiment data 150 may be determined based on audio from more than one turn 406. As described above, the sentiment data 150 may be expressed as one or more of a valence value, activation value, dominance value, and so forth. These values may be used to determine a single value, such as a tone value or sentiment index. The sentiment data 150 may include one or more index values 408, associated icons, associated colors, and so forth. For example, the combination of valence value, activation value, and dominance value, may describe a multidimensional space. Various volumes within this space may be associated with particular index values 408. For example, within that multidimensional space, a valence value of +72, activation value of 57, and dominance value of 70 may describe a point that is within a volume that is associated with the index value 408(1) which may be associated with a descriptor of "anxious".

In other implementations, other techniques may be used to determine sentiment data 150 from audio feature data 146 obtained from the second audio data 142. For example, a machine learning system comprising one or more of classifiers, neural networks, and so forth may be trained to associate audio features in the audio feature data 146 with particular index values 408, valence values, activation values, dominance values, associated icons, associated colors, and so forth.

Figure 5:
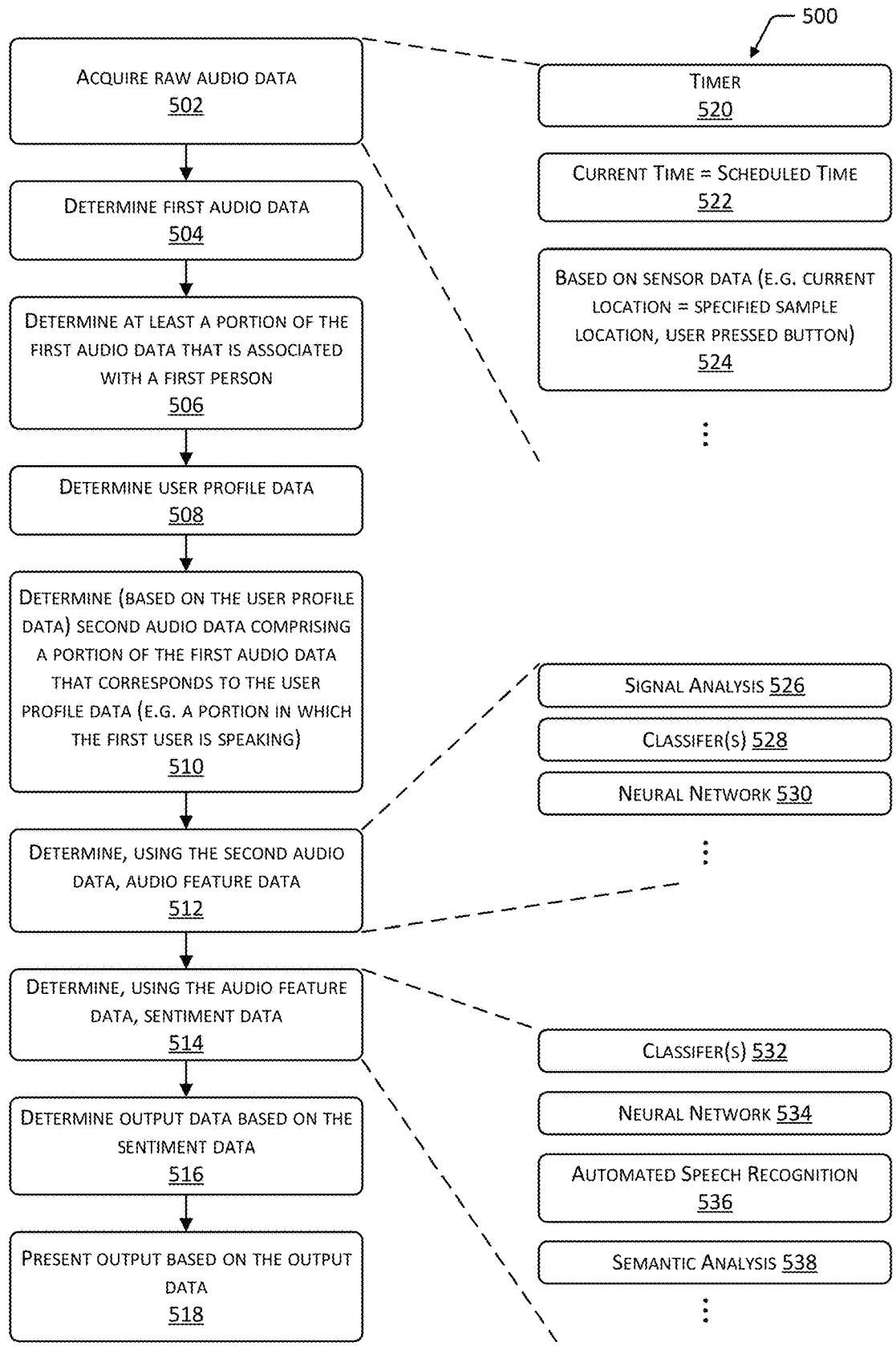
FIG. 5 illustrates a flow diagram of a process of presenting output based on sentiment data obtained from analyzing a user's speech, according to one implementation.

FIG. 5 illustrates a flow diagram 500 of a process of presenting output 164 based on sentiment data 150 obtained from analyzing a user's speech 116, according to one implementation. The process may be performed by one or more of the wearable device 104, the computing device 108, a server, or other device.

At 502 the raw audio data 118 is acquired. A determination may be made as to when to acquire the raw audio data 118. For example, the data acquisition module 322 of the wearable device 104 may be configured to operate the microphone array 112 and acquire the raw audio data 118 when a timer 520 expires, when a current time on the clock 306 equals a scheduled time as shown at 522, based on sensor data 128 as shown at 524, and so forth. For example, the sensor data 128 may indicate activation of a button 126(1), motion of the accelerometer 126(10) that exceeds a threshold value, input from a touch sensor 126(4), and so forth. In some implementations combinations of various factors may be used to determine when to begin acquisition of the raw audio data 118.

At 504 the first audio data 124 is determined. For example, the raw audio data 118 may be processed by the voice activity detector module 120 to determine if speech 116 is present. If no speech 116 is determined to be present, the non-speech raw audio data may be discarded. If no speech 116 is determined for a threshold period of time, acquisition of the raw audio data 118 may cease. The raw audio data 118 that contains speech 116 may be processed by the audio preprocessing module 122 to determine the first audio data 124. For example, a beamforming algorithm may be used to produce a microphone pattern 114 in which the signal to noise ratio for the speech 116 from the user 102 is improved.

At 506 at least a portion of the first audio data 124 that is associated with a first person is determined. For example, the turn detection module 136 may determine that a first portion of the first audio data 124 comprises the first turn 406(1).

At 508 user profile data 140 is determined. For example, the user profile data 140 for the user 102 registered to the wearable device 104 may be retrieved from storage. The user profile data 140 may comprise information that is obtained from the user 102 during an enrollment process. During the enrollment process, the user 102 may provide samples of their speech 116 that are then used to determine characteristics that are indicative of the user's speech 116. For example, the user profile data 140 may be generated by processing the speech 116 obtained during enrollment with a convolutional neural network that is trained to determine feature vectors representative of the speech 116, a classifier, by applying signal analysis algorithms, and so forth.

At 510, based on the user profile data 140, the second audio data 142 is determined. The second audio data 142 comprises the portion(s) of the first audio data 124 that is associated with the user 102. For example, the second audio data 142 may comprise that portion of the first audio data 124 in which a turn 406 contains a voice that corresponds within a threshold level to the user profile data 140.

At 512 the audio feature data 146 is determined using the second audio data 142. The audio feature module 144 may use one or more techniques, such as one or more signal analysis 526 techniques, one or more classifiers 528, one or more neural networks 530, and so forth. The signal analysis 526 techniques may determine information about the frequency, timing, energy, and so forth of the signals represented in the second audio data 142. The audio feature module 144 may utilize one or more neural networks 530 that are trained to determine audio feature data 146 such as vectors in a multidimensional space that are representative of the speech 116.

At 514 the audio feature data 146 is used to determine the sentiment data 150. The feature analysis module 148 may use one or more techniques, such as one or more classifiers 532, neural networks 534, automated speech recognition 536, semantic analysis 538, and so forth to determine the sentiment data 150. For example, the audio feature data 146 may be processed by a classifier 532 to produce sentiment data 150 that indicates a value of either "happy" or "sad". In another example, the audio feature data 146 may be processed by one or more neural networks 534 that have been trained to associate particular audio features with particular emotional states. The neural network 534 may provide output including, but not limited to, a valence value, activation value, dominance value, index value, and so forth.

The determination of the sentiment data 150 may be representative of emotional prosody. In other implementations the words spoken and their meaning may be used to determine the sentiment data 150. For example, the automated speech recognition 536 may determine the words in the speech 116, while the semantic analysis 538 may determine what the intent of those words is. For example, the use of particular words, such as compliments, profanity, insults, and so forth may be used to determine the sentiment data 150.

In some implementations the sentiment data 150 may include information that is used to rank or order at least a portion of the information in the sentiment data 150. For example, each of the index values 408 in the sentiment data 150 may be associated with one or more of a confidence value, dominance value, and so forth.

At 516 the output data 162 is determined based on the sentiment data 150. For example, the output data 162 may comprise instructions that direct a display device 134(3) to present one or more of the user interfaces described herein. The output data 162 may use the information indicative or ranking or ordering of the output 164 to determine what information to present, and in some implementations, where on the display device 134(3) to present the information. For example, the sentiment data 150 may include 20 different index values 408, each with an associated confidence value. The index values 408 may be sorted in descending order of the associated confidence value, and the top k index values 408 may be selected for presentation, where k is a non-zero positive integer. Continuing the example, the top three index values 408 or their associated descriptors may be included in the output data 162 for presentation. The relative arrangement of those descriptors may be determined at least in part based on the ranking. For example, the top ranked label or associated descriptor may be presented on the display device 134(3) at a location that is above the second ranked label or associated descriptor.

At 518 output 164 is presented based on the output data 162. For example, the user interface 166 is shown on the display device 134(3) of the computing device 108.

FIG. 6 is a block diagram 600 of the descriptor library 160 that associates index values 408 in the sentiment data 150 with descriptors 602 for presentation in the user interface 166, according to one implementation.

The descriptor library 160 provides an association between an index value 408 and one or more descriptors 602. The index values 408 may be associated with one or more emotional states. The index values 408 may comprise identifier strings, tokens, and so forth. The sentiment data 150 may include one or more index values 408.

The determination of a particular index value 408 may be somewhat imprecise, depending upon various factors. For example, an index value 408 may be associated with an emotional state with several different variations or nuances. The descriptor library 160 may provide a set of one or more descriptors 602 associated with the index value 408 that may be presented in the user interface 166. In some implementations, the descriptors 602 may comprise words that are deemed synonymous or equivalent to the emotional state described by the index value 408. For example, the label of "anxious" may be associated with descriptors such as "antsy", "edgy", "perturbed", and so forth.

In some implementations, the presentation module 156 may vary the descriptors 602 selected for the output data 162 and subsequent presentation on the display device 134(3) while the index value 408 remains constant. For example, if the index value 408 remains 408(1) for three consecutive sets of sentiment data 150, the descriptors 602 presented in the user interface 166 may first be "antsy", then "edgy", and then "perturbed". This presentation may be serial, in that "edgy" replaces "antsy" at a later time, and "perturbed" replaces "edgy" at a still later time.

This dynamic presentation of descriptors 602 associated with index values 408 provides several advantages. As mentioned above, the determination of the index values 408 may be imprecise. By presenting different descriptors 602, the user is provided a cue as to the emotional state, while the variation in the descriptors 602 presented provides a reinforcement of the idea that some uncertainty may exist in the process. Additionally, the dynamic presentation provides a visually engaging user interface 166 to the user 102. The changes to the descriptors 602 provide a change that may draw the eye of the user 102, and help them remain attentive to the user interface 166 and thus the emotional state they are presenting with at least their voice.

The descriptor library 160 is depicted as a table by way of illustration, and not necessarily as a limitation. In other implementations other data structures may be used.

Figure 7:
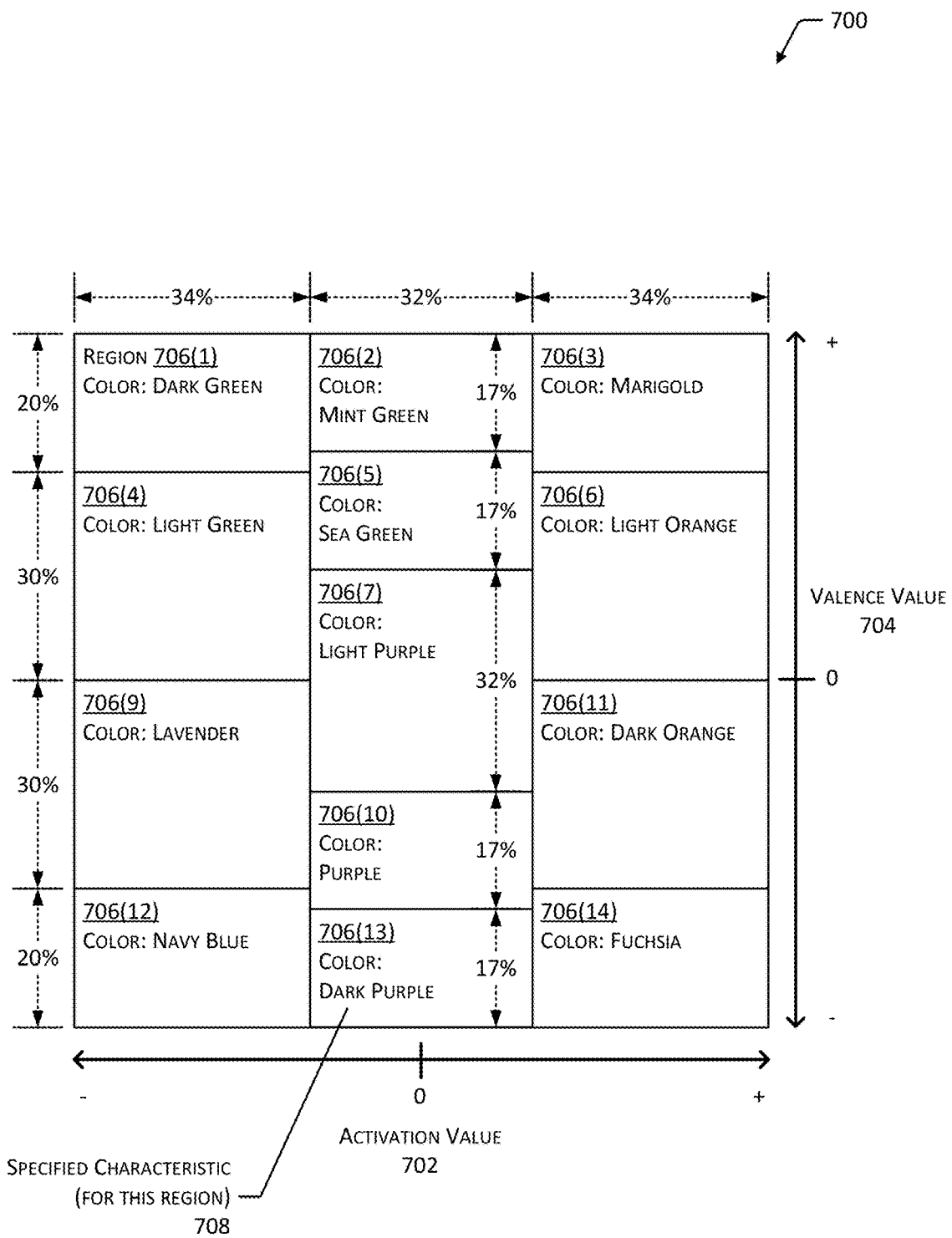
FIG. 7 is a diagram of regions in an emotional space and values for a specified characteristic, according to one implementation.

FIG. 7 is a diagram 700 of regions in an emotional space and values for a specified characteristic, according to one implementation. By way of illustration, and not necessarily as a limitation, an emotional space presented here has a first axis of activation value 702 and a second axis of valence value 704. Within this emotional space are depicted a plurality of regions 706. These regions 706 may be described in terms of the axes. For example, each region 706 in this illustration is associated with a particular range of activation values 702 and a particular range of valence values 704. While the regions 706 are presented here as abutting one another, in other implementations the regions 706 may not be in contact with one another. The regions 706 may be of different sizes and shapes within the emotional space, relative to one another.

A region 706 may be associated with one or more specified characteristics 708. The specified characteristics may be one or more of a color value, a luminance value, a shape designator, an animation designator, a blur effect value, a visual effect, and so forth. For example, the shape designator may indicate a particular shape or icon to be used when an indicator is associated with a region 706 or within that region 706.

In this illustration, each region 706 is associated with a specified characteristic 708 of a particular color. As described with regard to FIG. 9, the presentation of the indicator in the user interface 166 may be specified by the specified characteristic 708 of the region 706 that the indicator is associated with.

The regions 706 may be described or defined in other ways. For example, the regions 706 may describe an arrangement with respect to the user interface 166. Instead of dimensions with regard to the emotional space, the regions 706 may define areas within a user interface 166 for presentation on a display device 134(3).

Figure 8:
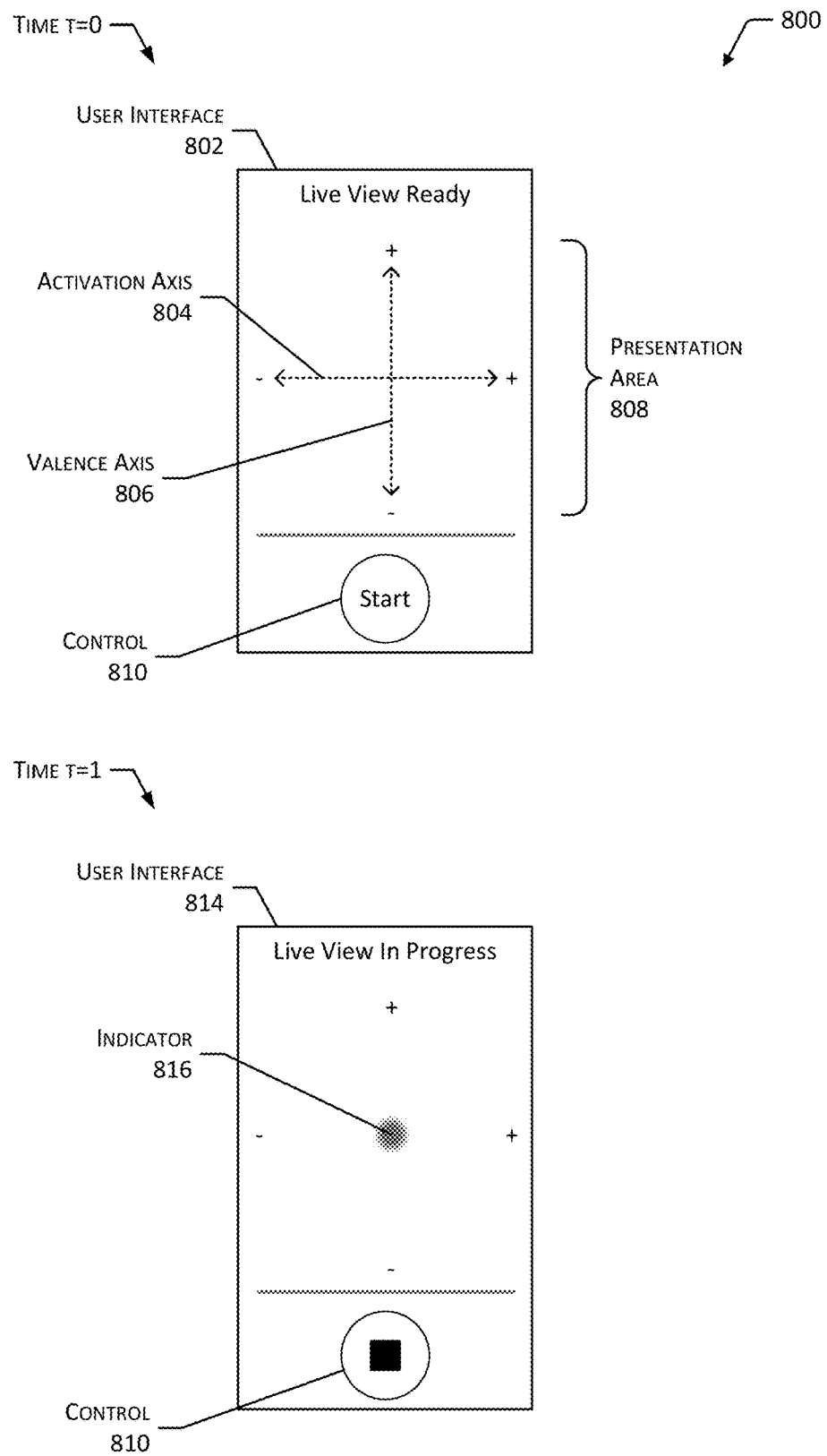
FIG. 8 illustrates user interfaces before determination of sentiment data and while waiting for sentiment data associated with a user, according to one implementation.

FIG. 8 illustrates user interfaces 800 before determination of sentiment data 150 and while waiting for sentiment data 150 associated with a user 102, according to one implementation. In the following figures, the labels indicative of time are provided for ease of illustration. It is understood that presentation of the user interfaces or particular aspects thereof may be performed in other orders. Unless otherwise specified, user interfaces are presented on one or more display devices 134(3).

At time t=0 a user interface 802 when no sentiment data 150 is available for presentation is shown. For example, time t=0 may correspond to the time before the user 102 has initiated operation of the system 100 to determine sentiment data 150.

Within the user interface 802 an activation axis 804 is arranged horizontally while a valence axis 806 is arranged vertically, that is perpendicular to the activation axis 804. A presentation area 808 includes the activation axis 804 and the valence axis 806. Also shown is a control 810. The control 810, when operated, may operate the system 100 to begin determining sentiment data 150, begin presentation of available sentiment data 150, stop determining sentiment data 150, and so forth.

At time t=1, a user interface 814 is shown in which the system 100 is ready to begin presenting information based on the sentiment data 150. A visual indicator (indicator) 816 is presented in this illustration beginning at the origin point of the activation axis 804 and the valence axis 806, here located within the center of the presentation area 808. In other implementations the origin point may be located in other positions with respect to the user interface 814.

In this illustration the indicator 816 is presented as a circle or dot. In other implementations other shapes, images, icons, animations, and so forth may be used.

At time t=1, the system 100 is idle, awaiting second audio data 142. For example, the user 102 has not been speaking at time t=1. The indicator 816 may provide information indicative of the idle state in one or more ways. For example, the color of the indicator 816 may be set to a particular value, such as "white" that indicates the user 102 is not currently being heard speaking. In another implementation, the indicator 816 may be presented as an animated visualization in which the apparent size of the indicator 816 increases and decreases, providing a visual effect of a pulsation. In another implementation a visual effect of a blur effect may be applied to the indicator 816, blurring the edges or outer area of the indicator 816. These implementations may be combined in various ways. For example, the idle state of the system may be presented in the user interface 814 as a white dot with blurred edges that pulsates.

The control 810 is also shown. As the system 100 is now operating, the control 810 may now be used to pause or stop operation of the system 100. For example, if at time t=1 the user 102 operates the control 810, the system 100 may stop acquiring raw audio data 118.

Figure 9:
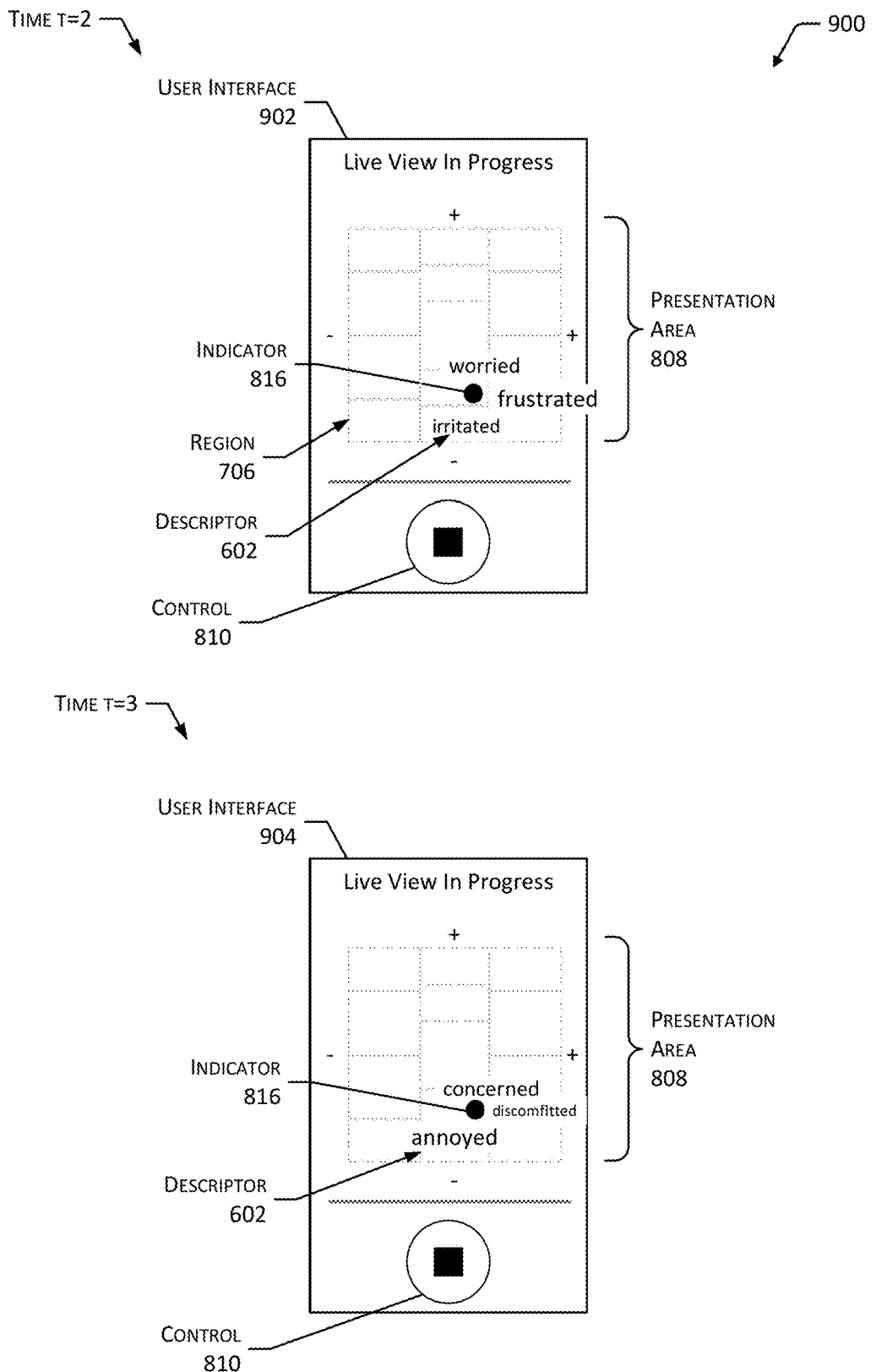
FIG. 9 illustrates user interfaces at different times showing that visual indicators and associated descriptors are changed to present a dynamic experience, according to one implementation.

FIG. 9 illustrates user interfaces 900 at different times showing indicators 816 and associated descriptors 602 are changed to present a dynamic experience, according to one implementation.

The user interface 902 is shown at time t=2. The system 100 has determined second audio data 142 and is providing sentiment data 150 associated with the speech of the user 102 before time t=2. The indicator 816 has been positioned in the presentation area 808 according to the values in the sentiment data 150 indicative of an activation value and a valence value. Also presented are one or more descriptors 602 associated with the indicator 816. In this implementation the descriptors 602 are adjacent to or within a threshold distance of a position of the indicator 816 in the user interface 902. In other implementations the descriptors 602 may be presented at other locations in the user interface.

One or more specified characteristics 708 of the indicator 816 may be determined based on the region 706, as described above. For example, the specified characteristic 708 may designate a particular color associated with the region 706. The indicator 816 as positioned within region 706(1) in this example may thus be presented with a color of "dark green". The regions 706 are depicted in this figure as dotted lines by way of reference, and may not be presented in the user interface 902 during use.

As described above, the descriptors 602 may be presented using various visual effects. For example, descriptors 602 may fade in and out using a fade effect. The order in which the descriptors 602 are presented with respect to one or more of the indicator 816 or other descriptors 602 may be based on information in the sentiment data 150. For example, index values 408 in the sentiment data 150 may have associated confidence values, ranking values, dominance scores, and so forth. In one implementation the descriptor 602(1) of a highest ranking index value 408(1) may be presented above the descriptor 602(2) of a second ranked index value 408(2) in the same set of sentiment data 150. For example, the sentiment data 150 may comprise the following information: {timestamp, activation value, valence value, dominance value, label1, label1 confidence value, label2, label2 confidence value, . . . }. For this example let label1="upset", label 1 confidence value=0.89, label2="annoyed", label 2 confidence value=0.71. Label1 is ranked higher than label2 due to the greater confidence value of 0.89 compared to 0.71.

Using the descriptor library 160, for the index value 408(1) the descriptors 602 given are "worried", "concerned", "distraught" and for the index value 408(9) the descriptors 602 given are "frustrated", "discomfited", "inconvenienced".

At time t=2, the presentation module 156 provides output data 162 in which the descriptor 602(1) for label1 is "worried" and the descriptor 602(2) for label2 is "frustrated". The presentation module 156 places the descriptor 602(1) for label1 above the descriptor 602(2) because label1 is higher ranked than label2.

In other implementations the placement in the user interface 902 may be determined based on other information. For example, a dominance value associated with each index value 408 may be used to determine the ranking and placement of the corresponding descriptors 602.

At time t=2 the indicator 816 may indicate that the user 102 is determined to be currently speaking by providing a visual effect. For example, the indicator 816 may be presented as a solid dot with no pulsation visual effect or blurring.

At time t=3 the sentiment data 150 has been refreshed. In this illustration, the label1 and label2 in the sentiment data 150 remain unchanged. However, the presentation module 156 has changed the corresponding descriptors 602. For example, "concerned" is now the descriptor 602 presented with respect to label1 while "discomfited" is presented with respect to label2. The change in descriptors 602 in the user interface 904 may be provided using one or more visual effects, such as a fade, swipe, slide, and so forth. For example, expired descriptors 602 may fade out, while new descriptors 602 fade in. In another example, old descriptors 602 may fade out while new descriptors "fly in" or appear to slide in from a location outside the user interface 904.

By changing the descriptors 602, even if the underlying index values 408 remain the same, the user interface 904 provides a dynamic and engaging experience. This assists the user 102 in maintaining their attention on the information presented in the user interface 904.

In one implementation the indicator 816 may not be presented. For example, the indicator 816 may only be presented if a first confidence value associated with the activation value is above a first threshold value and a second confidence value associated with the valence value is above a second threshold value. The descriptors 602 may also be omitted from presentation if a confidence value of the underlying index value 408 is less than a threshold value. Presentation of the indicator 816 may also be varied to indicate that one or more values are less than their associated confidence values. For example, a fade effect may be applied to the indicator 816, color may be change, shape may change, and so forth.

In some implementations sentiment data 150 that exhibits a change greater than a threshold value with respect to a previous sentiment data 150 may not be presented. For example, at a first time first sentiment data 150 indicates a first activation value and a first valence value. At a second time second sentiment data 150 indicates a second activation value and a second valence value. A distance may be determined between a first point described by the first activation value and the first valence value and a second point described by the second activation value and the second valence value. If that distance is greater than a threshold value, the second sentiment data 150 may not be presented. By omitting this data from presentation, the user interface may avoid presenting transitory changes in sentiment that may be confusing to the user 102.

Other types of output may be combined with the user interfaces described herein. For example, a haptic output may be provided to the user 102 by a haptic output device 134(1). Continuing the example, if one or more values in the sentiment data 150 exceed a threshold value, a haptic output may be provided to the user 102 to provide non-visual feedback.

Figure 10:
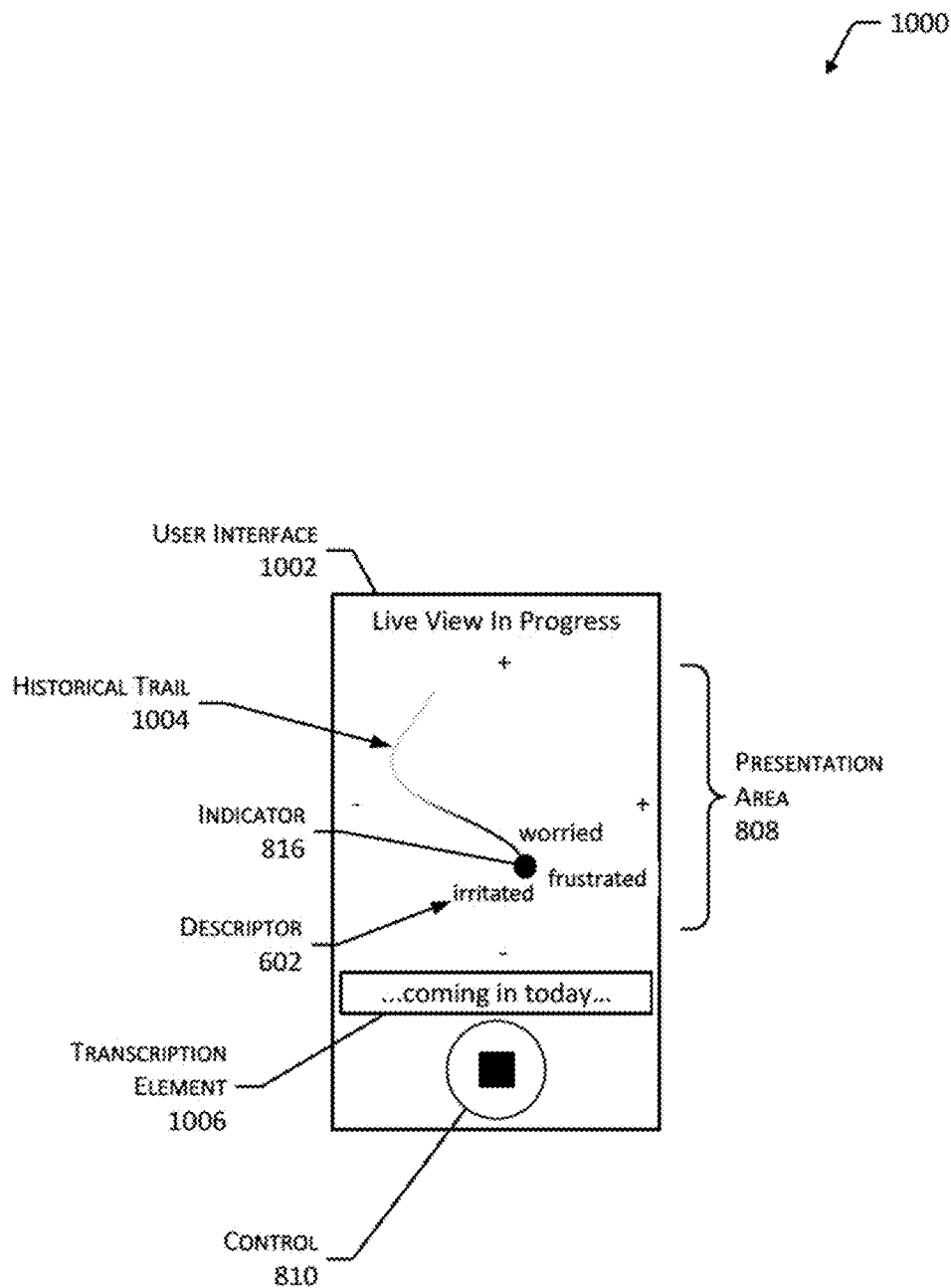
FIG. 10 illustrates a user interface in which a historical trail indicative of previous sentiment is shown, according to one implementation.

FIG. 10 illustrates at 1000 a user interface 1002 in which a historical trail 1004 indicative of previous sentiment is shown, according to one implementation.

In some situations, providing information about the sentiment data 150 immediately before the present may be useful to the user 102. For example, this may help the user 102 see how their speech has been changing over the last few seconds or minutes.

In this illustration, the user interface 1002 includes an indicator 816, such as described above. Also shown is a historical trail 1004 that extends away from a present position of the indicator 816 in the user interface 1002. In one implementation, the historical trail 1004 may be determined based on the historical data 334. In another implementation, previous coordinates within the presentation area 808 may be used to present the historical trail 1004.

Also shown in the user interface 1002 is a transcription element 1006. The transcription element 1006 may present transcription data obtained from an automated speech recognition (ASR) or other system that comprises a transcription of at least a portion of the speech 116 used to determine the sentiment data 150 that is currently being presented in the user interface 1002. For example, an automated speech recognition system (ASR) may be used to provide transcribed text that is shown in the transcription element 1006. Presentation of the transcribed text may assist the user 102 in better associating the emotional information shown in the user interface 1002 with a particular portion of their speech 116.

In some implementations the transcription element 1006 may present a specified portion of transcribed speech. In one implementation, the portion of transcribed speech that contains words associated with particular sentiments may be presented. For example, if the user 102 utters a phrase in which the dominance value exceeds a threshold value, the text corresponding to the portion of the phrase associated with that dominance value may be presented in the transcription element 1006. In another implementation, the portion of transcribed speech that contains specific words may be presented. For example, if the word "upset" has been stored as a word of interest, then the transcription element 1006 may present that word and some portion of the words before, after, or before and after that word. For example, the transcription element 1006 may present " . . . I am upset that you . . . ".

A visual effect of a fade for the historical trail 1004 that is based on time is shown. For example, as the sentiment data 150 indicated by the historical trail 1004 ages, it disappears from view in the user interface 1002.

In some implementations portions of the transcribed text may be placed adjacent to a corresponding portion of the historical trail 1004. For example, portions of transcribed text that correspond to a portion of the historical trail 1004 may be shown near that portion of the historical trail 1004, allowing the user 102 to see at least part of what was said and the sentiment conveyed by that speech 116.

Figure 11:
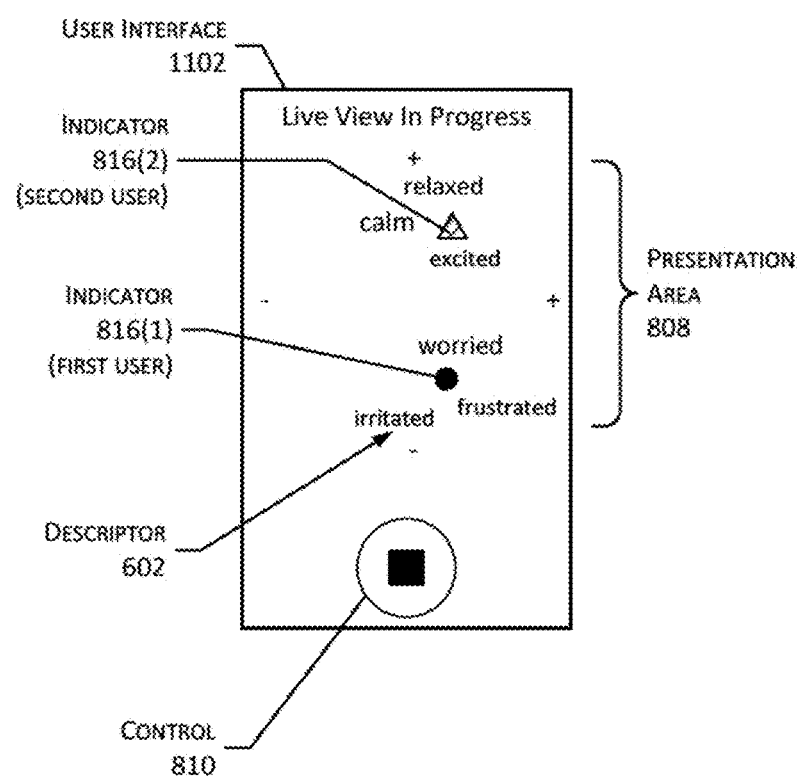
FIG. 11 illustrates a user interface in which indicators are presented contemporaneously for two different users, according to one implementation.

FIG. 11 illustrates at 1100 a user interface 1102 in which indicators 816 are presented contemporaneously for two different users 102, according to one implementation. For example, a first user 102(1) and a second user 102(2) may both be enrolled to use the system, and have corresponding user profile data 140. Both the first user 102(1) and the second user 102(2) have authorized operation of the system.

In the presentation area 808 of the user interface 1102, a first indicator 816(1) associated with the first user 102(1) is shown with associated descriptors 602. A second indicator 816(2) associated with the second user 102(2) is shown with associated descriptors 602. To facilitate the distinction as to which indicator 816 is associated with a particular user 102, indicators 816 associated with different users 102 may have different shapes, name labels may be presented, visual effects, and so forth. For example, as shown here the first indicator 816(1) is a circle while the second indicator 816(2) is a triangle.

Figure 12:
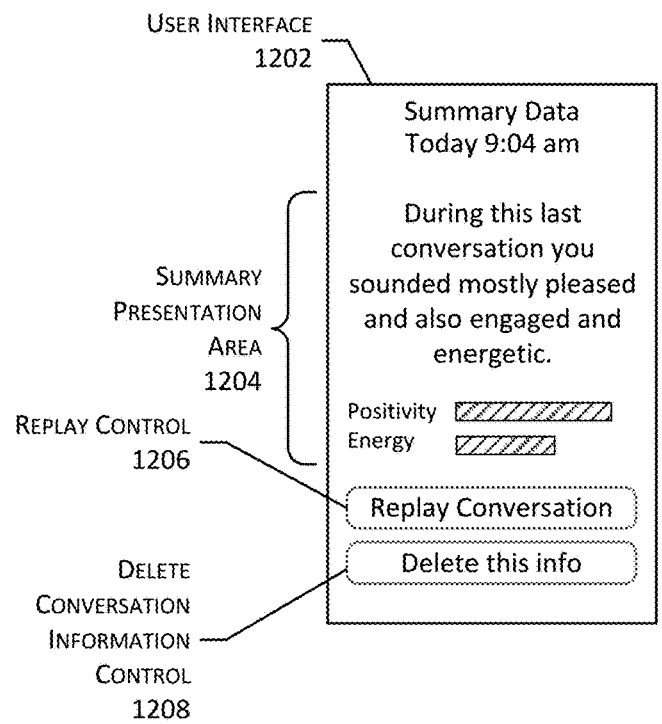
FIG. 12 illustrates a user interface in which summary data and controls are presented, according to one implementation.

FIG. 12 illustrates at 1200 a user interface 1202 in which summary data and controls are presented, according to one implementation. The user interface 1202 includes a summary presentation area 1204. The summary presentation area 1204 may provide information such as an overall characterization of the emotional state of the user 102 for some interval of time. For example, the interval of time may encompass the last conversation. In another example, the interval of time may be since some specified time, such as 12:00 a.m. The summary presentation area 1204 may include text, graphs, icons, and so forth.

A replay control 1206 allows the user 102 to replay all or a portion of the conversation.

Figure 13:
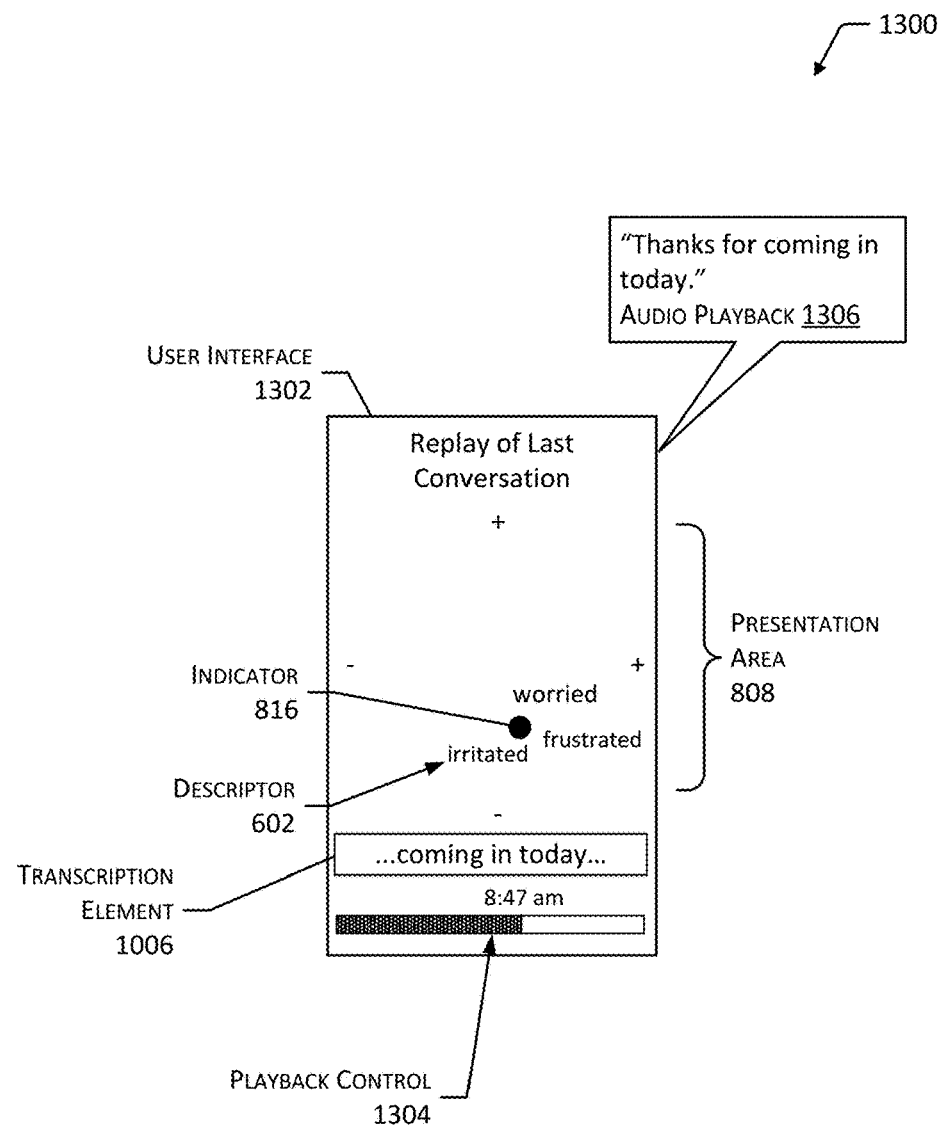
FIG. 13 illustrates a user interface in which a previous conversation is replayed with information about the sentiment during that conversation, according to one implementation.

FIG. 13 illustrates at 1300 a user interface 1302 in which a previous conversation is replayed with information about the sentiment during that conversation, according to one implementation. The user 102 may wish to replay a previous conversation to gain a better understanding of their emotional state during presentation. The user interface 1302 includes the presentation area 808, indicator 816, and associated descriptor 602. In some implementations the transcription element 1006 may present the transcribed speech 116 of the user 102 that is associated with a particular time in the replay. A playback control 1304 allows the user 102 to navigate through stored information about the previous conversation. For example, the playback control 1304 may allow the user 102 to "scrub" or shift the replay to an earlier or later time. In some implementations the replay may include presentation of stored audio. For example, audio playback 1306 of the conversation may be presented using an audio output device 134(2) such as a speaker.

The processes discussed herein may be implemented in hardware, software, or a combination thereof. In the context of software, the described operations represent computer-executable instructions stored on one or more non-transitory computer-readable storage media that, when executed by one or more processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described herein. The computer-readable storage medium may be one or more of an electronic storage medium, a magnetic storage medium, an optical storage medium, a quantum storage medium, and so forth. For example, the computer-readable storage media may include, but is not limited to, hard drives, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Thus, although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as illustrative forms of implementing the claims.

What is claimed is:

1. A method comprising:
   determining first sentiment data, wherein the first sentiment data is indicative of one or more characteristics of speech by a first user with respect to one or more dimensions;
   determining a first set of regions, wherein:
      each region is bounded by one or more ranges in the one or more dimensions,
      each region is a different size based on the one or more ranges, and
      each region is associated with a first specified characteristic;
   determining a first region from the first set of regions that the first sentiment data is associated with;
   determining, based on the first sentiment data, a first set of one or more descriptors;
   determining, based on the first set of one or more descriptors, a first label with a first confidence value;
   determining, based on the first set of one or more descriptors, a second label with a second confidence value;
   determining the first confidence value is greater than the second confidence value;
   determining a first descriptor from the first set of one or more descriptors that is associated with the first label;
   determining a second descriptor from a second set of one or more descriptors that is associated with the second label; and
   presenting with a display device at a first time:
      a first indicator at a first position on the display device based at least in part on the first sentiment data, wherein the first indicator is presented with the first specified characteristic associated with the first region,
      the first descriptor at a second position that is above the first position, and
      the second descriptor at a third position on the display device that is below the first position and the second position.

2. The method of claim 1, wherein the first specified characteristic is one or more of:
   a color value,
   a luminance value,
   a shape designator,
   an animation designator, or
   a blur effect value.

3. The method of claim 1, wherein:
   the first sentiment data is indicative of a first activation value and a first valence value;
   the first region is associated with a first range of activation values and a first range of valence values, and
   the first specified characteristic is a first color; and
   the determining the first region from the first set of regions that the first sentiment data is associated with comprising:
      determining the first activation value is within the first range of activation values and the first valence value is within the first range of valence values.

4. The method of claim 1, further comprising:
   determining that a threshold time has elapsed since the first time;
   determining no sentiment data associated with the first user has been determined since the first time; and
   presenting with the display device at a second time:
      a second indicator at the first position on the display device with a second specified characteristic.

5. The method of claim 1, further comprising:
   determining second sentiment data, wherein the second sentiment data is indicative of one or more characteristics of speech by a second user with respect to the one or more dimensions;
   determining a second region from the first set of regions that the second sentiment data is associated with;
   determining, based on the second sentiment data, a second set of one or more descriptors; and
   presenting with the display device at the first time:
      a second indicator at a fourth position on the display device based at least in part on the second sentiment data, wherein the second indicator is presented with the first specified characteristic associated with the second region, and a third descriptor from the first set of one or more descriptors on the display device at a fifth position.

6. The method of claim 1, further comprising:
determining transcription data indicative of words in the speech by the first user that corresponds with the first sentiment data; and
presenting with the display device at the first time:
at least a portion of the transcription data.

7. The method of claim 1, further comprising:
determining historical coordinate data indicative of previous positions on the display device of indicators presented before the first time; and
presenting with the display device at the first time:
a historical trail indicating at least a portion of the previous positions.

8. The method of claim 1, wherein the one or more dimensions are indicative of a dominance value that is representative of rise and fall patterns of pitch of voice of the first user over time; and
the method further comprising:
determining a first dominance value associated with the first descriptor of the first set of one or more descriptors;
determining a second dominance value associated with the second descriptor of the first set of one or more descriptors;
determining the first dominance value is greater than the second dominance value; and
wherein presenting the second descriptor at the third position is further based on that the first dominance value is greater than the second dominance value.

9. The method of claim 1, further comprising:
determining, at a second time after the first time, summary data that is based at least in part on the first sentiment data; and
presenting with the display device after the second time:
information based on the summary data that characterizes an emotional state of the first user during an interval of time that is between the first time and the second time.

10. A system comprising:
a first memory storing first computer-executable instructions; and
a first hardware processor that executes the first computer-executable instructions to:
determine first sentiment data, wherein the first sentiment data is indicative of one or more characteristics of speech by a first user with respect to one or more dimensions;
determine a first set of regions, wherein each region is bounded by one or more ranges in the one or more dimensions, and further wherein each region is associated with a specified value of a first specified characteristic;
determine a first region from the first set of regions that the first sentiment data is associated with;
determine, based on the first sentiment data, a first set of one or more descriptors;
determine historical coordinate data indicative of previous coordinates within a user interface of indicators presented before a first time, wherein each of the previous coordinates are with respect to a first axis and a second axis; and
present, within the user interface at the first time:
a historical trail indicating at least a portion of the previous coordinates of a first indicator,
the first indicator at a first coordinate within the user interface based at least in part on the first sentiment data, wherein the first indicator is presented with the specified value of the first specified characteristic that is associated with the first region, and
at a second coordinate within the user interface, a first descriptor from the first set of one or more descriptors.

11. The system of claim 10, wherein the specified value of the first specified characteristic is indicative of one or more of:
a color value,
a luminance value,
a shape designator,
an animation designator, or
a blur effect value.

12. The system of claim 10, wherein:
the first sentiment data is indicative of a first activation value and a first valence value;
the first region is associated with a first range of activation values and a first range of valence values; and
the specified value of the first specified characteristic is a first color; and
the instructions to determine the first region from the first set of regions that the first sentiment data is associated with comprise instructions to:
determine the first activation value is within the first range of activation values and the first valence value is within the first range of valence values.

13. The system of claim 10, the first computer-executable instructions to:
determine that a threshold time has elapsed since the first time;
determine no sentiment data associated with the first user has been determined since the first time; and
present within the user interface at a second time a second indicator at the first coordinate within the user interface with a second specified value of the first specified characteristic.

14. The system of claim 10, wherein the first sentiment data comprises a first label with a first confidence value and a second label with a second confidence value; and
the first computer-executable instructions to:
determine that the first confidence value is greater than the second confidence value;
determine that the first descriptor is associated with the first label;
determine that a second descriptor is associated with the second label; and
present within the user interface at the first time the second descriptor at a third coordinate within the user interface that is below the first coordinate.

15. The system of claim 10, the first computer-executable instructions to:
determine second sentiment data, wherein the second sentiment data is indicative of one or more characteristics of speech by a second user with respect to the one or more dimensions;
determine a second region from the first set of regions that the second sentiment data is associated with;
determine, based on the second sentiment data, a second set of one or more descriptors; and
present within the user interface at the first time:
a second indicator at a third coordinate within the user interface based at least in part on the second sentiment data, wherein the second indicator is presented with a second specified value of the first specified characteristic associated with the second region, and a second descriptor from the second set of one or more descriptors within the user interface at a fourth coordinate.

16. The system of claim 10, wherein the one or more dimensions are indicative of a dominance value that is representative of rise and fall patterns of pitch of voice of the first user over time; and the first computer-executable instructions to:
determine a first dominance value associated with the first descriptor of the first set of one or more descriptors;
determine a second dominance value associated with a second descriptor of the first set of one or more descriptors;
determine the first dominance value is greater than the second dominance value; and
present within the user interface at the first time:
the second descriptor from the first set of one or more descriptors at a third coordinate within the user interface that is below the second coordinate.

17. The system of claim 10, the first computer-executable instructions to:
determine, at a second time after the first time, summary data that is based at least in part on the first sentiment data; and
present, within the user interface after the second time:
information based on the summary data about an emotional state of the first user during an interval of time that is between the first time and the second time.

18. A method comprising:
determining first sentiment data, wherein the first sentiment data is indicative of one or more characteristics of speech by a first user with respect to one or more dimensions;
determining a first set of regions, wherein each region is bounded by one or more ranges in the one or more dimensions, and further wherein each region is associated with a specified value of a first specified characteristic;
determining a first region from the first set of regions associated with the first sentiment data;
determining, based on the first sentiment data, a first set of one or more descriptors;
determining historical coordinate data indicative of previous coordinates within a user interface of indicators presented before a first time, wherein each of the previous coordinates are with respect to a first axis and a second axis; and
determining instructions to present:
a historical trail indicating at least a portion of the previous coordinates of a first indicator,
the first indicator at a first coordinate within the user interface based at least in part on the first sentiment data, wherein the first indicator is presented with the first specified characteristic associated with the first region, and
a first descriptor from the first set of one or more descriptors within the user interface at a second coordinate.

19. The method of claim 18, wherein the first sentiment data comprises a first label with a first confidence value and a second label with a second confidence value; and
the method further comprising:
determining that the first confidence value is greater than the second confidence value;
determining that the first descriptor is associated with the first label;
determining that a second descriptor is associated with the second label; and
generating instructions to present the second descriptor at a third coordinate within the user interface that is proximate to the first coordinate.

20. The method of claim 18 wherein the one or more dimensions are indicative of a dominance value that is representative of rise and fall patterns of pitch of voice of the first user over time; and
the method further comprising:
determining a first dominance value associated with the first descriptor of the first set of one or more descriptors;
determining a second dominance value associated with a second descriptor of the first set of one or more descriptors;
determining the first dominance value is greater than the second dominance value; and
presenting within the user interface at the first time:
the second descriptor from the first set of one or more descriptors at a third coordinate that is below the second coordinate.

* * * * *